US006684754B2

(12) United States Patent  
Comer

(10) Patent No.: US 6,684,754 B2
(45) Date of Patent: Feb. 3, 2004

(54) PNEUMATIC MUSCLE ANALOGS FOR EXOSKELETAL ROBOTIC LIMBS AND ASSOCIATED CONTROL MECHANISMS

(76) Inventor: Alan Elbert Comer, P.O. Box 1134, Olalla, WA (US) 98359

(*) Notice: Subject to any disclaimer, the term of this patent is extended or adjusted under 35 U.S.C. 154(b) by 7 days.

(21) Appl. No.: 10/193,035

(22) Filed: Jul. 10, 2002

(65) Prior Publication Data

US 2003/0018388 A1 Jan. 23, 2003

Related U.S. Application Data

(60) Provisional application No. 60/304,469, filed on Jul. 10, 2001.

(51) Int. Cl.[7] .............................. F15B 13/00; B25J 11/00
(52) U.S. Cl. ............................... 91/534; 92/92; 92/137; 901/21; 901/22
(58) Field of Search ............................. 91/534; 92/92, 92/137, 91, 90; 623/26; 901/21, 22, 28, 9

(56) References Cited

U.S. PATENT DOCUMENTS

| 2,211,478 A | 8/1940 | Pierce | |
| 2,483,088 A | 9/1949 | De Haven | |
| 4,944,755 A | * 7/1990 | Hennequin et al. | 623/26 |
| 5,021,064 A | 6/1991 | Caines | 623/26 |
| 6,067,892 A | 5/2000 | Erickson | 92/92 |

* cited by examiner

Primary Examiner—Edward K. Look
Assistant Examiner—Michael Leslie

(57) ABSTRACT

Artificial muscle analog 1000 is located within hollow exoskeletal bone 10. Muscle 1000 comprises inflatable bladder 120, cable 130, roller 140, anchor point 150, and connection means 160 whereby said bladder may be inflated and deflated. Bladder 120 is affixed to the interior surface of said bone. Cable 130, attached to bone 10 at point 150, passes over bladder 120 and through roller 140. Cable 130, if unobstructed and taut, takes a shortest path from point 150 to roller 140. When inflated, bladder 120 forces cable 130 to deviate from this shortest path, pulling cable 130 in through said roller, under tension. In their paired opposing muscle form 2000, the artificial muscles synergistically assist each other when used in opposition. Paired muscles 2000 may actuate a robotic arm 3000, and are easily controlled by the associated simple low-cost control systems 100a,b,c of the present invention.

20 Claims, 9 Drawing Sheets

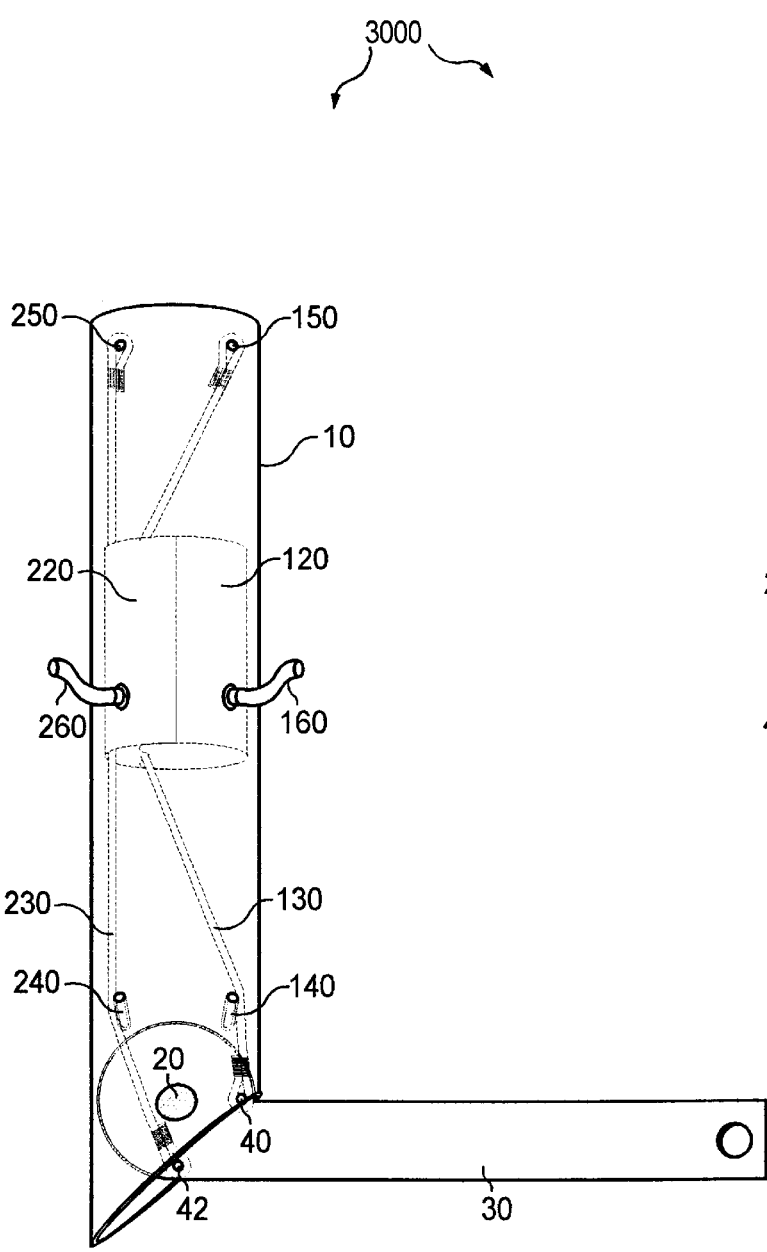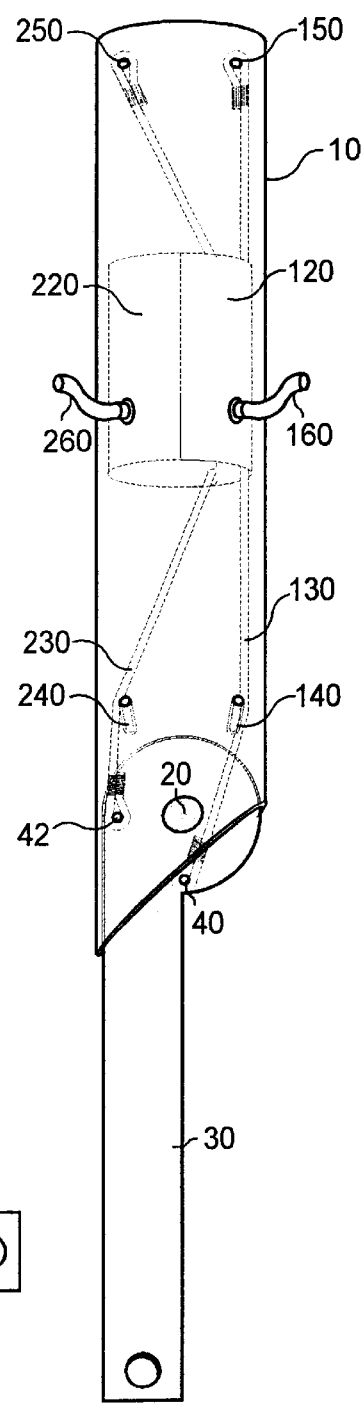
FIG. 3a
FIG. 3b

PNEUMATIC MUSCLE ANALOGS FOR EXOSKELETAL ROBOTIC LIMBS AND ASSOCIATED CONTROL MECHANISMS

CROSS-REFERENCE TO RELATED APPLICATIONS

This application claims the benefit of Provisional Patent Application Ser. No. 60/304,469 filed Jul. 10, 2001.

FEDERALLY SPONSORED RESEARCH

Not Applicable

SEQUENCE LISTING OR PROGRAM

Not Applicable

BACKGROUND

1. Field of Invention

The present invention relates to mechanical actuators. More specifically, the present invention relates to artificial muscle analogs which do not rely on electromagnetism for their motive force. Certain aspects of the present invention relate to robust, low-cost exoskeletal limbs powered by such muscle analogs, which have applications in many fields including robotics or prosthetics. A final aspect of the present invention relates to a particularly simple means of controlling such exoskeletal limbs, using a novel electro-pneumatic feedback loop.

2. Description of Prior Art

Historically, machines have been invented using an almost endless array of different mechanical methods to induce physical movement.

In recent years, however, most such machines have been based on some form of electromagnetic force, especially electrical motors. In some cases, this has been due more to the overwhelming prevalence of electricity and especially the electrical motor as a motive device, rather than the inherent superiority of this approach for the particular problem. Although an electrical motor is arguably the best solution for many problems, especially those requiring rotary motion, other situations exist where alternate approaches have inherent advantages. Yet relatively little research has been done into other motive methods, due in part to the tremendous popularity of the electrical motor.

One situation where an electromagnetic actuator is not particularly ideal is when a relatively-slow, controlled but powerful linear actuation is desired, especially when the desired machine must copy biological motion. For example, consider what is needed to build a mechanical limb that mimics a human arm. First limiting consideration only to the major biceps and triceps muscles used for flexion and extension of the arm, respectively, one requires a pair of "muscle analogs" or artificial muscles which can each contract with hundreds or thousands of kilograms of force, yet which weigh only a few kilograms. The muscle analogs should each be capable of pulling a "tendon analog" or cable through several centimeters of travel. Ideally, the muscle analogs should be adjustable in their "pull" throughout the range of motion. A feedback mechanism should be available so that the mechanical limb can be held at any position throughout the range of motion. And to best mimic biological muscles, the available pulling force on the cable should be greatest when the muscle analog is extended, falling as the muscle contracts; this tendency offsets the reduced mechanical advantage inherent in biological jointed limbs at extension.

The characteristics of a typical electrical motor are not well suited for such an application. For a variety of reasons, a power-conversion assembly is generally required to convert the output power of the motor to a usable form. First, the rotary motion is not desired, and must be converted to a linear motion through the addition of further hardware such as gears or threaded shafts. Also, a typical motor has optimal performance at a higher RPM than is desirable for such an application, so further speed-reducing gearing is also required. And since a powerful actuation is desired, the gearing used to reduce the speed and linearize the motion must efficiently take advantage of the mechanical advantage involved in such a speed reduction. Finally, an electrical motor does not exert force unless it is drawing power; so if it is desired to maintain an actuator in a particular position once it is moved there, some further hardware in the form of a braking means is also required. And the weight of this overcomplicated solution, including the electrical motor, the associated power-conversion assembly, and braking means, can be substantial. Clearly, there are inherent disadvantages in using electrical motors for such applications.

Specialized motors, such as stepper motors, are sometimes used for such applications, since they can generally run at slower speeds, closer to the desired speed of such actuators. But these are even more complicated and expensive to make than standard motors. And stepper motors are generally a less powerful form of electric motor; so if the stepper motor is run at a slow speed without speed-reduction/force-increasing gearing, a motor large enough to develop sufficient force will generally be even heavier than a more-typical motor with its associated gearing.

Solenoids would seem to be a better fit than motors for use as such a linear actuator, since they are inherently linear in function. A solenoid is an electromagnetic coil which pulls a ferrous core or piston into the coil's center when current is allowed to flow. However, solenoids are also relatively heavy and inefficient for a given strength, and again they require power to hold their position. And solenoids tend to be "digital" in nature, since the pull of the solenoid actually increases as the piston is pulled in. The maximum strength of the pull is at the wrong end of the motion, resulting in biologically-unnatural jerky motions which tend to accelerate toward an abrupt stop. And, using a typical solenoid, there is no good way to stop the motion partway, or lock the solenoid in a partially-closed position.

With these inherent problems using electromagnetic force, alternate approaches have been investigated and indeed are used today in certain instances of linear actuation.

For example, one novel approach uses "memory-wire" which changes length and/or shape when a current is passed through it. Such muscle analogs are extremely simple, light and small. However, this technology is still primarily a lab curiosity, since the available force is very small and the power efficiency is quite low.

Other non-electromagnetic approaches in the prior art have been more successful. For example, hydraulic cylinders enjoy a dominant role where the linear actuation desired must be particularly powerful. A hydraulic cylinder is a piston/cylinder arrangement wherein a piston is forced out when a essentially-incompressible pressurized fluid is allowed to enter a cylinder chamber when a control valve is opened. Double acting hydraulic cylinders are also available, wherein two opposing chambers are present so that the piston can be forced out or pulled in, in order to achieve the desired motion, a user opens the appropriate control valves to pressurize one chamber while simultaneously venting the opposing chamber to an unpressurized fluid reservoir. In a hydraulic cylinder, the available force is essentially constant throughout the range of motion, dependent only on the pressure of the fluid and the cross-sectional area of the piston. And since the fluid is incompressible, hydraulic cylinders lock the actuator solidly in position when all the appropriate valves are closed. However, hydraulic cylinders are generally quite slow and heavy, and are used only when the desired motion need not be particularly fast.

Analogously, pneumatic cylinders are sometimes used, with compressed air or other gases replacing the essentially incompressible but comparatively viscous hydraulic fluid in a hydraulic cylinder. Such pneumatic cylinders generally actuate much faster than comparable hydraulic cylinders. Double acting pneumatic cylinders are also available, able to exert force both during extension and retraction by pressurizing one chamber and venting the opposing chamber (probably to the atmosphere if compressed air is used). And, like hydraulic cylinders, the available force is essentially constant through the range of motion, dependent only on the gas pressure and the piston cross section. However, since the fluid now used is a compressed gas which is not incompressible in any sense, the actuator does not truly "lock" in place when the valves are closed. Instead, the pneumatic cylinder acts more like a spring, with an increasing force opposing deviation from the desired actuator position. This is actually more akin to biological muscle force than a truly-locking actuator. Of course, like a spring, there may be oscillations in the actuator positioning if appropriate damping is not included in the design. Pneumatic cylinders are generally used at considerably lower pressures than hydraulic cylinders due in part to the greater danger associated with compressed gases compared to pressurized fluids. Pneumatic cylinders are thus usually considerably less powerful than an hydraulic cylinder of similar size; however, since they can therefore be built less strongly, and since their fluid is a gas rather than a liquid, pneumatic cylinders are also typically much lighter than their hydraulic counterparts.

Hydraulic and pneumatic cylinders have some limitations in common. Both require seals, machining and close tolerances in their manufacture, and are therefore relatively expensive to make. And both require cleanliness and care in their use. In particular, the mirror-smooth machined surface of the piston (which is often exposed when the actuator is extended) must not be bent, scratched or roughened if the cylinder is to function properly. Even microscopic particles introduced into the hydraulic fluid, for example, can score this surface and ruin a cylinder; so high-quality filtration of the pressurized fluid is necessary. Such limitations can cause problems for cylinders used as actuators in a dirty or abrasive environment, or where the actuator may be subjected to impacts or other abuse.

Still, of the available widely-used technologies in the prior art, pneumatic cylinders represent the closest match for use as muscle analogs. Although less force is produced than for a hydraulic cylinder of similar size, this force is yet sufficient to mimic biological strength. This has led to the investigation of other embodiments of pneumatic muscle analogs besides the simple piston/cylinder arrangement.

One rarely-seen type of pneumatic actuator which would seem to be particularly appropriate for use as a muscle analog is the class of devices collectively known as McKibben artificial muscles. These are cylindrically symmetric devices comprising an expandable, rubberlike bladder or balloon enclosed within a sheath loosely woven in diagonal patterns from relatively-unstretchable fibers which connect at the ends to tendon analogs; the sheath resembles a familiar "chinese finger puzzle". When the bladder is inflated, the woven sheath is forced to expand in diameter around the bladder and therefore must contract in length, pulling on the tendon. Such a device has most of the advantages of a single-acting pneumatic cylinder, with much less weight and a less expensive manufacturing process; no metal or machining is generally required.

Like a pneumatic cylinder, the actuation can be held in place by closing a valve through which compressed fluid is introduced into the balloon. Of course, since a McKibben muscle only pulls in one direction, this will only oppose further motion in the same direction. However, even this aspect is much like a biological muscle, where a pair of opposing muscles (like the biceps and triceps in a human arm) are required to hold a lever (the forearm) in a given position. A pair of McKibben muscles, appropriately mounted, can replace a double acting pneumatic cylinder in most applications, with a considerable reduction in weight. The range of motion, force and distribution of force through the range of motion are all fairly close to the biological equivalents in an human arm; and the weight of these muscle analogs is even less than equivalent biological muscles.

Actuators like the McKibben artificial muscle have been known for decades. Unfortunately, however, there are practical problems with this technology which have limited the popularity of these devices and kept them from widespread use. First, the functionality of the McKibben muscle is dependent on quite special physical properties required of the enclosed bladder. Actuating the muscle requires the bladder to expand from its resting size to a much-larger inflated diameter; this requires the bladder material to be stretched several times its resting dimensions. Each actuation of the muscle requires a separate expansion of the bladder. Thus, the bladder material of a McKibben muscle must be stretchable without damage many thousands of times over a period of years, in order to achieve reliability equivalent to competing technologies. And although in some instances such long-term reliability has been achieved with other inventions using stretchable materials, such as rubber inner tubes, the material has generally not been required to expand and contract so many times, or so near its elastic limit. For example, an inner tube is typically inflated only a few times in a lifetime of use, and is supported within a toroidal chamber formed by its enclosed wheel and the semi-rigid tire surrounding it, once inflated. And typically, the minor radius of this toroidal chamber is not significantly larger than the minor radius of the inner tube before the rubber begins to stretch; so the rubber in an inner tube is not required to expand near its elastic limit in use. The rubber inner tube is a successful idea because the material property actually required of the rubber is reliable flexibility through generally low-amplitude deviations from a prescribed shape, centered around an operating point much below the elastic limit of the material. This property is much easier to attain than reliable flexibility through unsupported high-amplitude stretching near the elastic limits of a material.

In practice, it is difficult or impossible to find materials which are capable of reliably stretching so far, so many times. According to recent publications, the best and most reliable material known for the bladder in a McKibben muscle is still natural latex rubber; so essentially no advances in materials for this application have been made in the decades since its invention. Clearly, the McKibben muscle suffers from reliability problems brought on by its dependence on remarkable material properties which are difficult or impossible to realize. The few commercial manufacturers of McKibben muscles today are usually unwilling to provide even an estimate of the life expectancies of their products, which puts them in an unfavorable light when their products are compared with competing technologies that provide not only estimates but guarantees of reliability.

Further, despite the advantages inherent in its design, the McKibben muscle has never achieved wide acceptance, possibly due to this difficulty in producing materials which can deliver reliability even approaching the reliability of competing technologies. And even though the design is simple in concept, the materials typically used inexpensive, and the manufacturing process simple, McKibben muscles are not significantly less expensive than competing, more-reliable technologies. In fact, McKibben muscles commercially available today are comparable or greater in price than comparable pneumatic cylinders, even with their expensive and complex machined metal design.

And the McKibben muscle is somewhat difficult to work with. In some ways, it resembles a biological muscle too well. For example, it is a relatively fragile structure, even more so than a protoplasmic muscle (which does not fail if punctured with a pin); yet it lacks the self-healing mechanisms which make biological structures so reliable. Instead, it requires protection from a hostile environment. A robust protective chamber built around the structure is required if the user wants to ensure that the bladder is not punctured and that the woven cover is not frayed. Yet enough room must be allowed for the bladder to inflate in order for the artificial muscle to work correctly.

And when McKibben muscles are used to drive a mechanical limb, rigid support members to mimic the bones of the limb must be present, and are often hollow. Yet the McKibben muscle does not recognize the existence or take advantage of these coexisting structures, despite its need for protection. In short, the McKibben muscle closely mimics endoskeletal biological muscles, but its need for protection and relative unreliability have kept it from becoming significant in the marketplace.

Objects and Advantages

Accordingly, several objects and advantages of the present invention are:

1. To provide a linear actuator which mimics an organic muscle.
2. To provide a muscle analog with strength comparable or greater than that of an organic muscle of similar size.
3. To provide a muscle analog with speed comparable to that of organic muscles.
4. To provide a muscle analog capable of pulling a cable through a range of motion similar to that of an organic muscle.
5. To provide a muscle analog whose force throughout its range of motion decreases from a maximum at extension, like an organic muscle.
6. To provide a muscle analog which is lightweight and compact.
7. To provide a simple, low-cost and easily-manufacturable muscle analog.
8. To provide a muscle analog which does not rely on electric motors or other forms of electromagnetic force for its motive power.
9. To provide a muscle analog which is capable of holding at positions intermediate through its range of motion, without drawing power.
10. To provide a muscle analog which does not require materials with unusual, exotic or difficult to attain material properties.
11. To provide a muscle analog with high reliability.
12. To provide a muscle analog which synergistically uses coexisting structural elements as part of its own design.
13. To provide a simple, low-cost method of building robust, reliable exoskeletal robotic limbs.
14. To provide a simple, low-cost method of controlling exoskeletal robotic limbs.

SUMMARY

A novel artificial muscle, designed to be enclosed within a substantially-rigid substantially hollow member, pipe or exoskeletal bone 10, advantageously chosen from among coexisting structural elements, comprises a bladder 120, an artificial tendon or cable 130, and a low-friction cable-positioning means or roller 140, affixed so as to constrain said cable to move freely longitudinally along a first side of the pipe interior. Said bladder is placed inside the pipe and affixed along said first side of the pipe interior. Cable 130 is attached along said first side of said pipe, at a point of attachment 150 placed longitudinally past the bladder. The cable passes from point of attachment 150 over bladder 120 and through low-friction cable-positioning means 140. A hose 160 is attached to bladder 120, through which the bladder may be inflated or deflated. When the bladder is deflated, the cable runs in an essentially straight line over the deflated bladder, along said first side of the pipe interior. When the bladder is subsequently inflated, it forces the portion of the cable passing over the bladder toward the opposing side of the pipe interior, which pulls cable 130 in through the low-friction cable-positioning means.

DRAWINGS

Drawing Figures

FIG. 1*a* is a diagram showing artificial muscle 1000 of the present invention in the relaxed state, mounted within pipe 10 with bladder 120 deflated and cable 130 extended.

FIG. 1*b* is a diagram showing artificial muscle 1000 of FIG. 1*a* in the flexed state, with bladder 120 inflated, pulling in cable 130.

FIG. 2*a* is a diagram showing two artificial muscles of the present invention mounted in opposing positions within the same pipe, both relaxed, with both bladders deflated and cables extended.

FIG. 2*b* is a diagram showing the two opposing artificial muscles of FIG. 2*a* with bladder 120 inflated, bladder 220 deflated, cable 130 pulled in, and cable 230 extended.

FIG. 2*c* is a diagram showing the two opposing artificial muscles of FIG. 2*a* with bladder 220 inflated and bladder 120 deflated, so that cable 230 is pulled in and cable 130 is extended.

FIG. 3*a* is a diagram of an exoskeletal robotic arm 3000 of the present invention, which incorporates the structure of FIG. 2*b* as the upper arm, and adds a pivotally-mounted forearm section, controlled by the muscle analogs. In this diagram, as in FIG. 2*b*, bladder 120 is inflated and bladder 220 deflated, so that cable 130 is pulled in and cable 230 is extended. This state results in the arm assembly being in the bent position.

FIG. 3*b* is a diagram of exoskeletal robotic arm 3000 of the present invention with the arm extended. In this diagram, as in FIG. 2*c*, bladder 120 is deflated and bladder 220 inflated, so that cable 230 is pulled in and cable 130 is extended.

FIG. 4*a* is a diagram showing the symbol used to represent prior-art 5-port, 2-position valve 50.

FIG. 4*b* is a diagram showing how valve 50 might be connected to control robotic arm 3000.

FIG. 4*c* is a diagram showing the symbol used to represent prior-art 5-port, 3-position valve 50*a*.

Figure 5A:
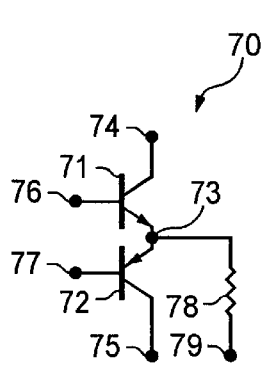
Figure 5B:
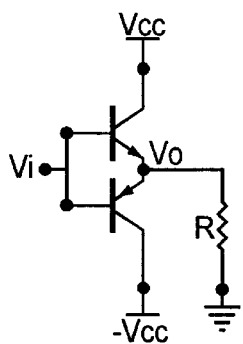
Figure 5C:
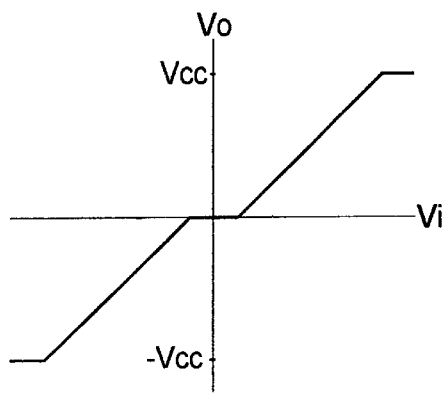
Figure 6A:
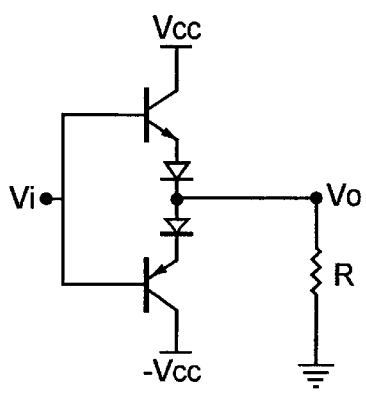
Figure 6B:
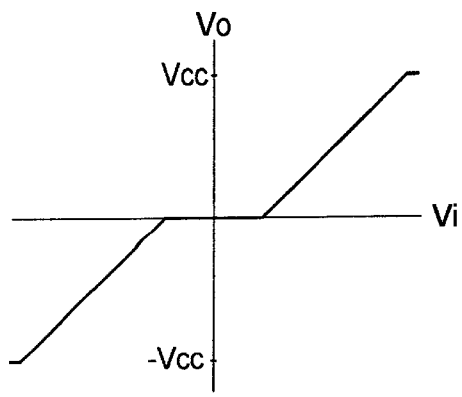
Figure 7:
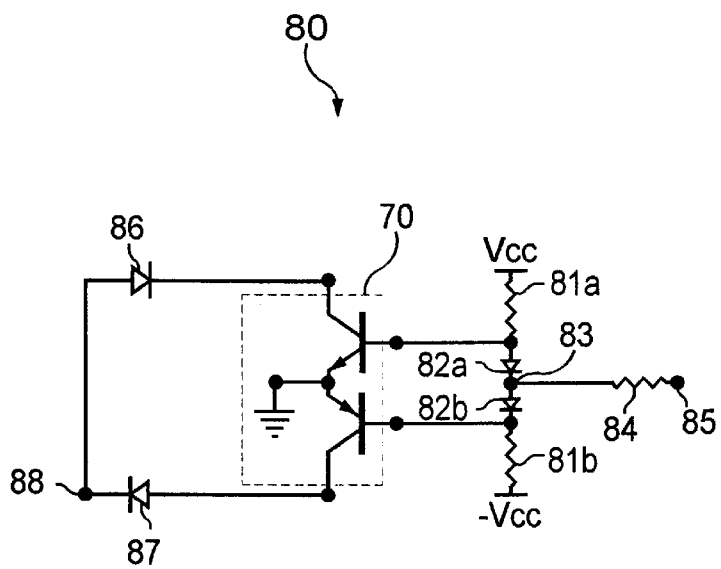
Figure 8:
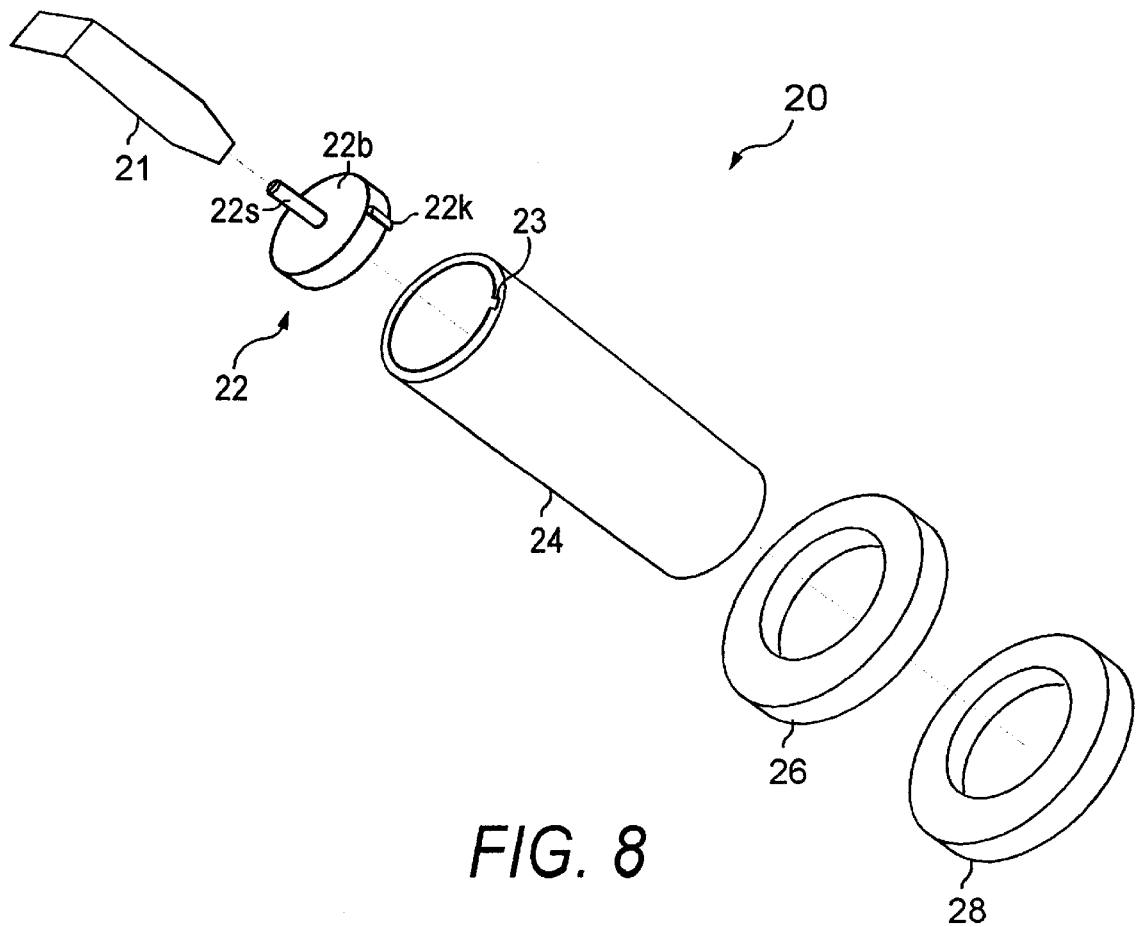

FIG. 5a is a schematic circuit diagram of a prior-art bipolar 2-transistor push-pull cell FIG. 5b is a schematic circuit diagram of the push-pull cell of FIG. 5a connected in a standard common-base configuration, forming a well-known prior-art class B output stage FIG. 5c shows the expected transfer characteristic of the circuit depicted in FIG. 5b; note the characteristic "flat spot" which results in the familiar crossover distortion of such a circuit FIG. 6a is a simplified schematic circuit diagram of a slightly-modified class B output stage FIG. 6b shows the expected transfer characteristic of the circuit depicted in FIG. 6a, with an even larger "flat spot" in the transfer characteristic FIG. 7 is a circuit diagram showing another configuration of the push-pull cell of FIG. 5a; this circuit is useful in controlling solenoid valves FIG. 8 is an expanded view of pivot assembly 20 of robotic arm 3000

Figure 9A:
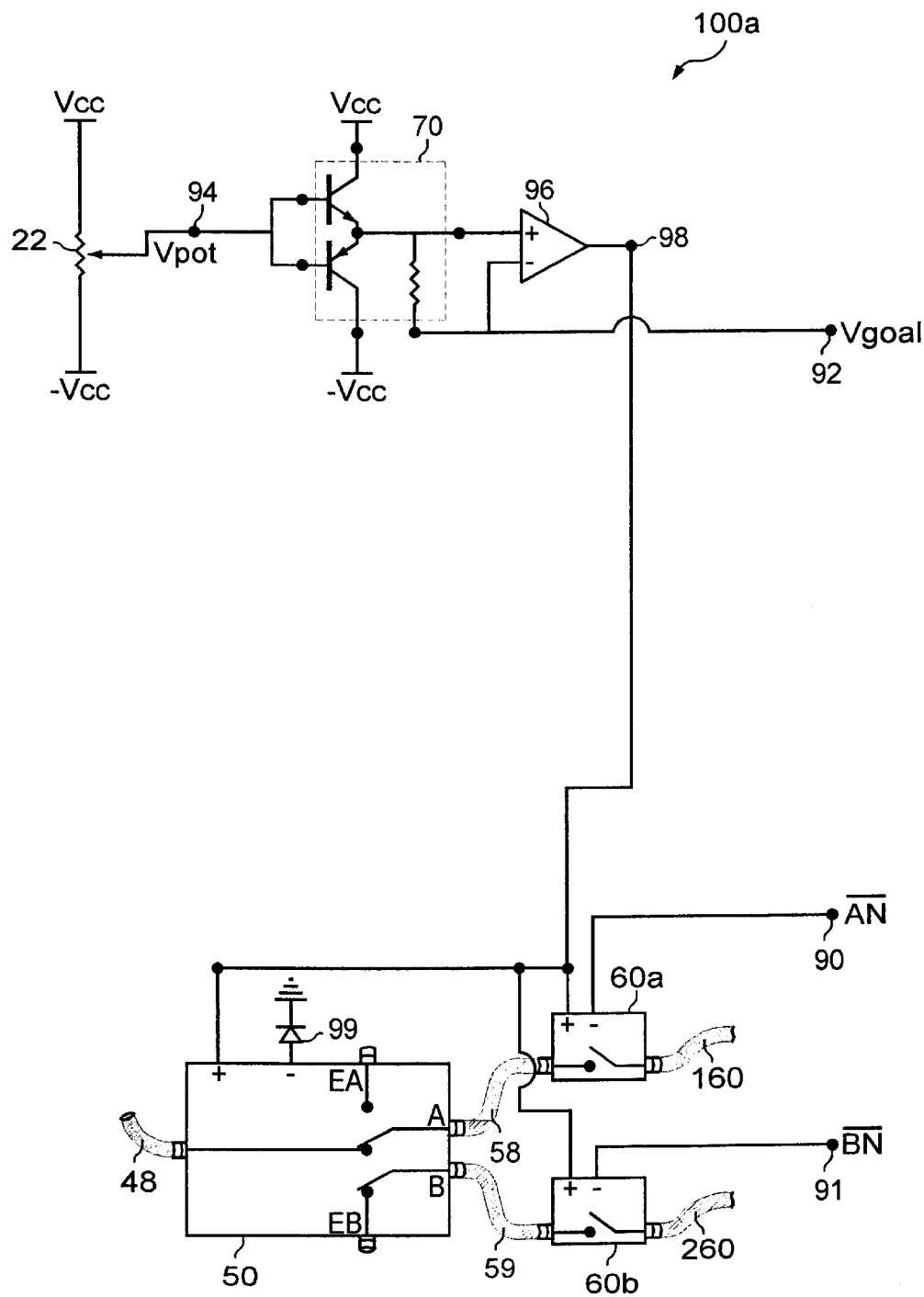

FIG. 9a is a schematic diagram of a novel pneumatic control system 100a for the paired opposing muscle analogs within robotic arm 3000; this version is best for a system with intensive computer or operator supervision.

Figure 9B:
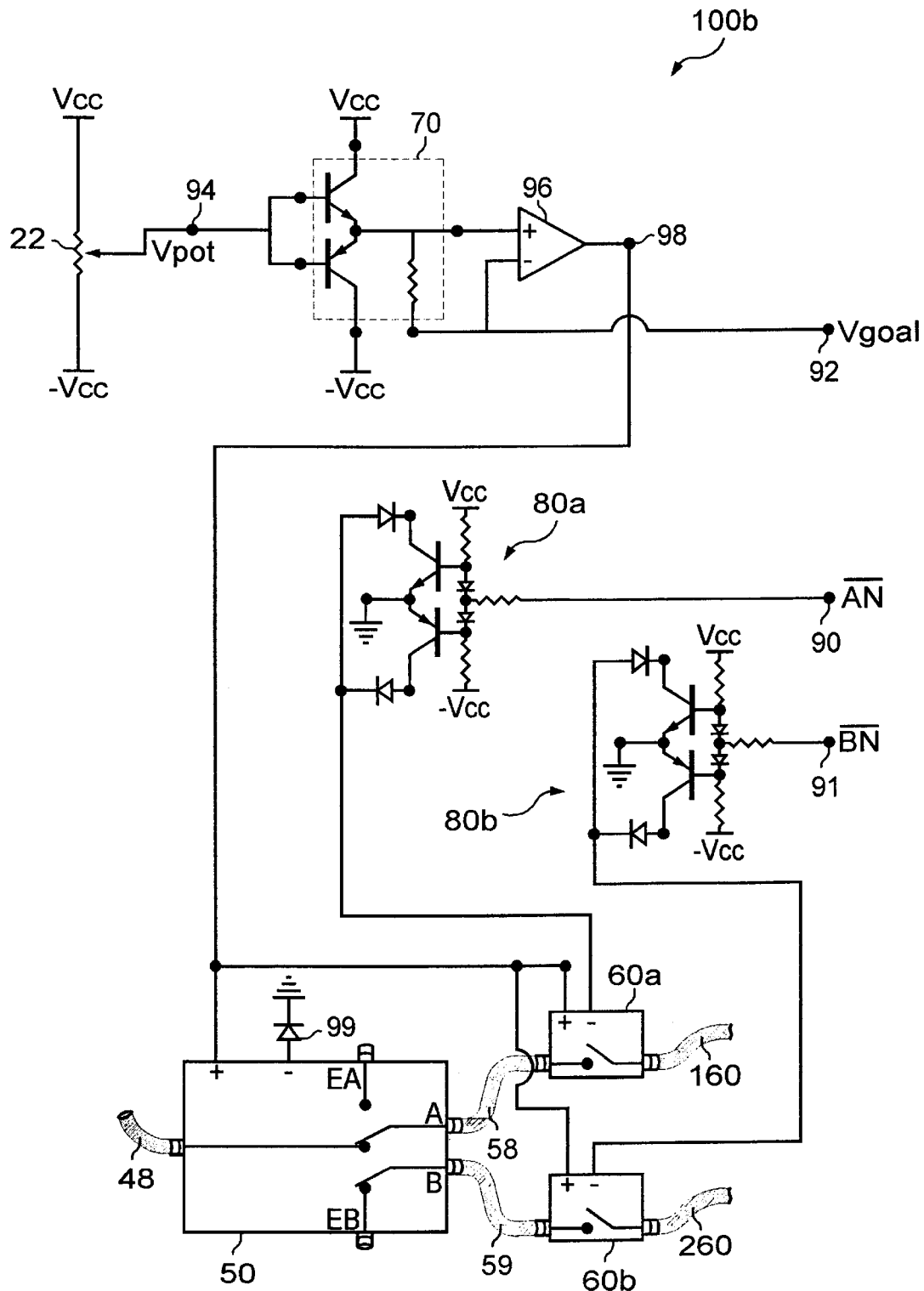

FIG. 9b is a schematic diagram of a novel pneumatic control system 100b for the paired opposing muscle analogs within robotic arm 3000; this version is best for a system with little computer or operator supervision.

Figure 9C:
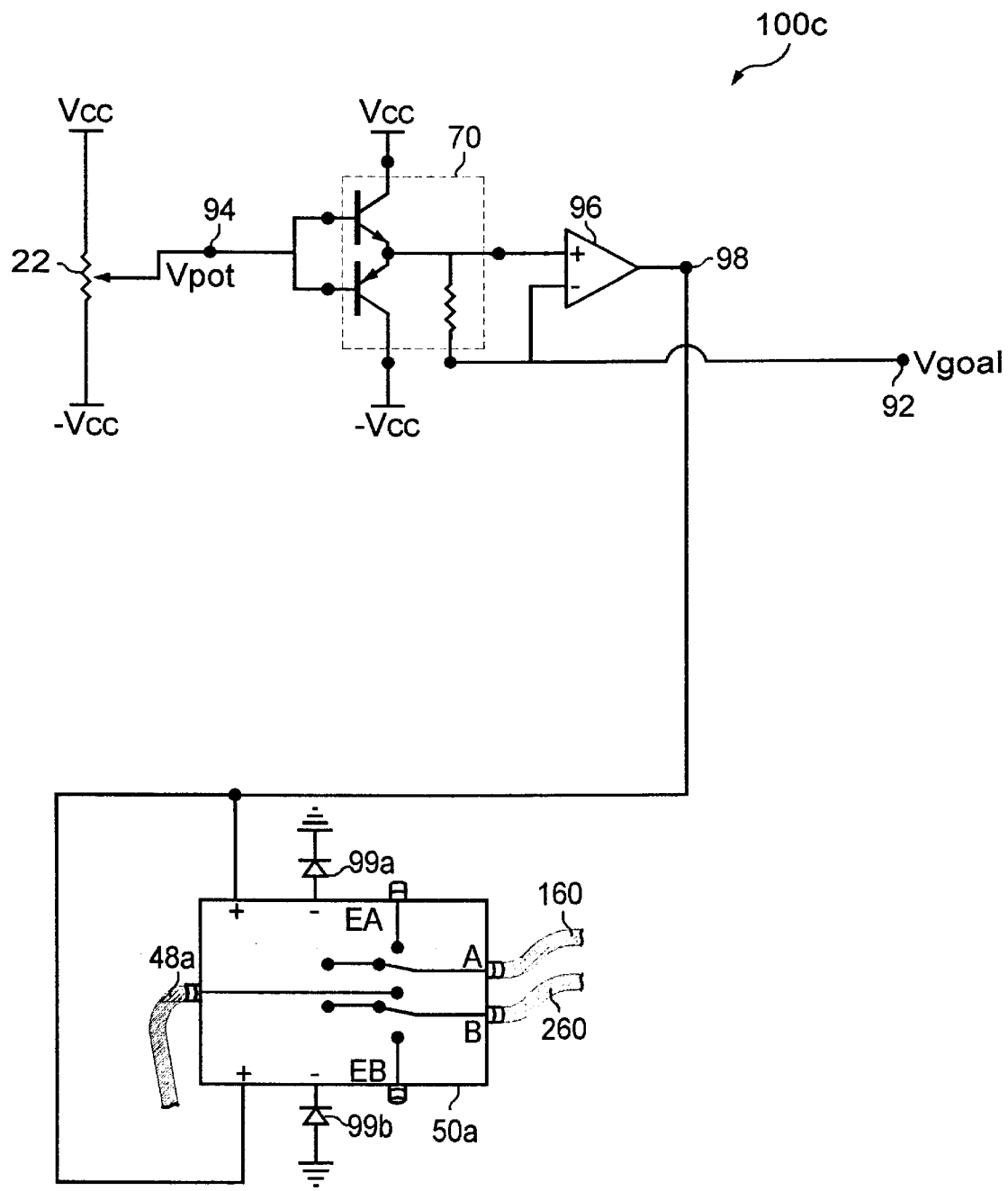

FIG. 9c is a schematic diagram of a novel hydraulic control system 100c for the paired opposing muscle analogs within robotic arm 3000; this simplified version may be used if the pressurized fluid is essentially incompressible.

Reference Numerals in Drawings

10 Substantially-rigid hollow structural member, pipe or exoskeletal bone containing the artificial muscle
20 Pivot forming elbow joint of robotic arm 3000
21 L-shaped screwdriver-headed member attached to pipe 10, mated with slotted stem 22s of potentiometer 22
22 Potentiometer physically mounted within pivot 20 of robotic arm 3000
22b Body of potentiometer 22
22k Key on body 22b which mates with keyway 23 inside pivot shell 24
22s Stem of potentiometer 22
23 Keyway inside pivot shell 24 which mates with key 22k
24 Tubular pipelike pivot shell of pivot 20
26,28 Bearing assemblies attached to pipe 10 for mounting pivot 20
30 Forearm of robotic arm 3000
40 Attachment point where artificial tendon 130 connects to forearm 30
42 Attachment point where artificial tendon 230 connects to forearm 30
48 Pressurized fluid intake hose to port 51 of valve 50
48 a Pressurized fluid intake hose to port 51a of valve 50a
50 5-port 2-position valve
51 Pressurized fluid inlet port of valve 50
52 First (A) outlet port of valve 50
53 Second (B) outlet port of valve 50
54 First (EA) exhaust port of valve 50
55 Second (EB) exhaust port of valve 50
56 Positive (+) control terminal of valve 50
57 Negative (−) control terminal of valve 50
58 Hose connecting port 52 of valve 50 to port 61 of valve 60a
59 Hose connecting port 53 of valve 50 to port 61 of valve 60b
50a 5-port 3-position valve
51a Pressurized fluid inlet port of valve 50a
52a First (A) outlet port of valve 50a
53a Second (B) outlet port of valve 50a
54a First (EA) exhaust port of valve 50a
55a Second (EB) exhaust port of valve 50a
56a Positive (+) control terminal of 1st solenoid in valve 50a
57a Negative (−) control terminal of 1st solenoid in valve 50a
56b Positive (+) control terminal of 2nd solenoid in valve 50a
57b Negative (−) control terminal of 2nd solenoid in valve 50a
60,60a,60b Identical 2-port 2-position normally-closed valves
61 Pressurized fluid inlet port of valve 60
62 Outlet port of valve 60
66 Positive (+) control terminal of valve 60
67 Negative (−) control terminal of valve 60
70 Prior-art bipolar 2-transistor push-pull circuit
71 NPN transistor in circuit 70
72 PNP transistor in circuit 70
73 Common-emitter output terminal of circuit 70
74 Collector terminal of NPN transistor 71 in circuit 70
75 Collector terminal of PNP transistor 72 in circuit 70
76 Base terminal of NPN transistor 71 in circuit 70
77 Base terminal of PNP transistor 72 in circuit 70
78 Output load resistor in circuit 70, connected between terminals 73,79
79 Reference terminal of load resistor 78 in circuit 70
80,80a,80b Identical valve-control circuits containing push-pull circuit 70
81a,b Identical bias resistors in circuit 80
82a,b Identical bias diodes in circuit 80
83 Node between two identical bias diodes 82a,b in circuit 80
84 Input resistor linking input terminal 85 to node 83 in circuit 80
85 Input control terminal of circuit 80
86,87 Current-path diodes in circuit 80
88 Output terminal of circuit 80
90,91 Terminals where control signals allowing actuation of 1st and 2nd opposing muscle analogs, respectively, enter improved control systems 100a,b
92 Terminal of analog voltage Vgoal controlling position of robotic arm 3000
94 Wiper connection terminal of potentiometer 22
96 Amplifier/Buffer
98 Output node of amplifier 96
99,99a,99b Identical rectifying diodes
100a Computer-driven pneumatic control system of the present invention
100b Pneumatic control system requiring little computer intervention
100c Simple hydraulic control system of the present invention
120 Bladder of first muscle analog
130 Tendon of first muscle analog
140 Low friction cable-positioning means or roller of first muscle analog
150 Point at which the end of tendon 130 is affixed to pipe 10

160 Hose through which fluid enters or leaves bladder 120
220 Bladder of second (opposing) muscle analog
230 Tendon of second (opposing) muscle analog
240 Low friction cable-positioning means for second muscle analog
250 Point at which the end of tendon 230 is affixed to pipe 10
260 Hose through which fluid enters or leaves bladder 220
1000 Entire artificial muscle assembly with single muscle
2000 Entire artificial muscle assembly including two opposing muscles
3000 Entire exoskeletal robotic arm assembly, including and powered by assembly 2000

DETAILED DESCRIPTION

Although the familiar mammalian endoskeletal muscle structure is perhaps more attractive to many researchers, an exoskeletal arrangement is more practical for machines, even for machines designed to mimic biological motion. The artificial muscle, robotic arm and control system of the present invention together provide a practical, low-cost method of building robust, reliable exoskeletal robotic machines capable of lifelike motion.

Figure 1A:
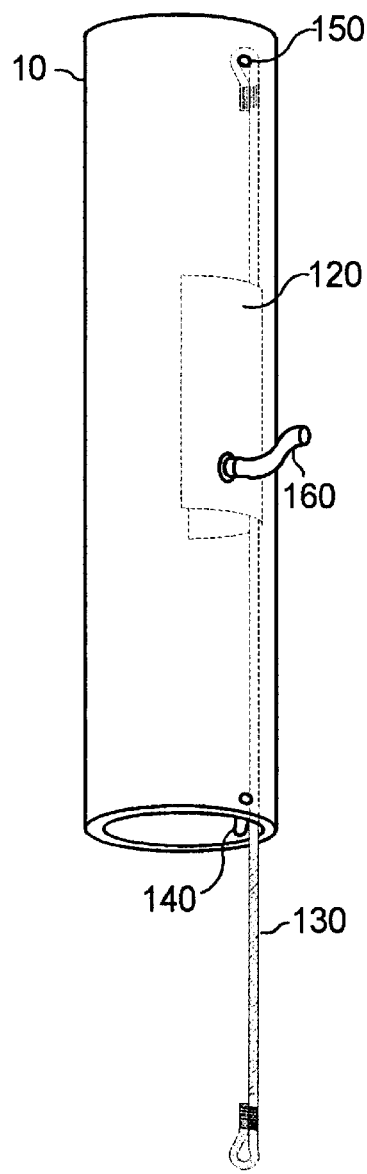

Description—FIG. 1a—Single Artificial Muscle

A novel artificial muscle assembly 1000 is formed within a substantially-rigid robust substantially hollow member, pipe or exoskeletal bone 10, which encloses the artificial muscle structure and protects the more fragile elements of the muscle structure which will be mounted within. Advantageously, pipe 10 is synergistically chosen from among those structural members already present in the design wherein the muscle will be used; so this massive component is not truly a part of the artificial muscle system but instead merely represents a single "bone" or part of the skeletal structure that the muscle works upon.

And building structures using such hollow pipelike structural elements is no hardship. Geometrical considerations dictate that for maximum strength, structural members should not have a cross-section which is a closed solid, in any case. For example, solid round bars or solid rectangular beams of structural steel are rarely seen, a pipe or I-beam formed of the same material and having the same weight will have superior rigidity and other enhanced structural properties, and will be easier to work with. And structural member with both enclosed and open non-solid cross-sections are widely available for comparable prices. So when a designer is faced with a choice between: 1) hollow structural members such as pipes with enclosed circular cross sections or beams with enclosed square or rectangular cross sections; and 2) structural members with open cross sections such as I-beams, U-beams or L-beams; it is easy for the designer to simply choose the hollow alternative. And in any case, for any artificial muscle technology which might benefit from protection from a potentially hostile environment, which in general includes all technologies which are not already enclosed, the protective endoskeletal structure will always be preferable.

Artificial muscle 1000 comprises a bladder 120, an artificial tendon or cable 130, and a low-friction cable-positioning means or roller 140, all mounted within bone 10 so that an exoskeletal muscle structure is formed. Roller 140 is affixed so as to constrain said cable to move freely longitudinally along a first side of the bone interior. According to a presently-preferred embodiment, bladder 120 is advantageously shaped like a section of hose with closed ends, and is placed inside the bone and affixed along said first side of the bone interior. Cable 130 is attached along said first side of said bone, at a point of attachment 150 placed longitudinally on the far side of the bladder from cable-positioning means 140. Artificial muscle 1000 is designed so that cable 130 passes from point of attachment 150 over bladder 120 and through low-friction cable-positioning means 140. And since cable 130 must be able to slide across the surface of bladder 120 as it inflates or deflates, an optional flexible low-friction protective cable sheath (not shown) might advantageously be affixed along the entire length of bladder 120, with cable 130 passing through the sheath. Many such protective sheaths have been seen in the prior art, such as those commonly seen on 10-speed bicycles which contain the brake and shift cables.

Artificial muscle 1000 further comprises a hose 160 connected to bladder 120, forming means for introducing and removing pressurized fluids to/from bladder 120; hose 160 may pass through the wall of bone 10 to connect with bladder 120 if desired, as shown for simplicity in FIGS. 1a,b. However, more in keeping with the endoskeletal theme of this design, hose 160 can alternatively be attached to the bladder inside bone 10, so that it may run inside the bone and be protected thereby.

According to a presently-preferred embodiment, bladder 120 has an inflated cross-section chosen to approximately equal the inner cross-section of the bone so that when the bladder is inflated, the bone supports the bladder sides along the bone interior. This ensures that the material forming said bladder need not stretch, but must only be flexible; in fact, according to a presently-preferred embodiment, the bladder should not be significantly stretchable A possible alternative is to enclose a bladder, formed either of stretchable material or unstretchable material, within a non-stretching sheath which closely matches the configuration of the inflated bladder, so that the bladder is completely supported when inflated by the fully-expanded sheath; again, passageways must be left for tendon 130 and hose 160. This configuration most closely matches the example previously given of an inner tube within a tire, which is a well-understood and mature prior-art technology long known to provide long-term reliability when built with commonly available, low cost materials. And if no protective cable sheath is used to contain tendon 130 as it passes over bladder 120, such a non-stretching sheath might advantageously be formed of a hard-wearing and low-friction material such as a steel belt or Kevlar mesh, perhaps with a teflon coating.

However, this alternative merely represents a "bladder within a bladder" assembly wherein the inside bladder forms the seal, and the outside bladder holds the pressure; and this assembly itself is not significantly stretchable. For the purposes of the present invention, such an assembly can be considered in its entirety simply as a single, non-stretching bladder with particularly desirable physical properties.

Optionally, a rigid chamber closely matching the configuration of the inflated bladder might be formed in the bone around the bladder, so that the bladder is completely supported when inflated except for passageways left for tendon 130 and hose 160. However, such a supporting chamber becomes necessary only when the bladder material is significantly stretchable; robust, flexible yet not significantly stretchable materials which can hold significant pressure yet maintain their flexibility over long periods of time already exist, such as the materials used in firehoses. And only the ends of the bladder actually need to support the pressure, since the walls of the bone support the inflated bladder on all sides. So for the artificial muscle of the present invention, such a rigid chamber is not truly necessary.

Operation—FIGS. 1a,b—Single Artificial Muscle

Figure 1B:
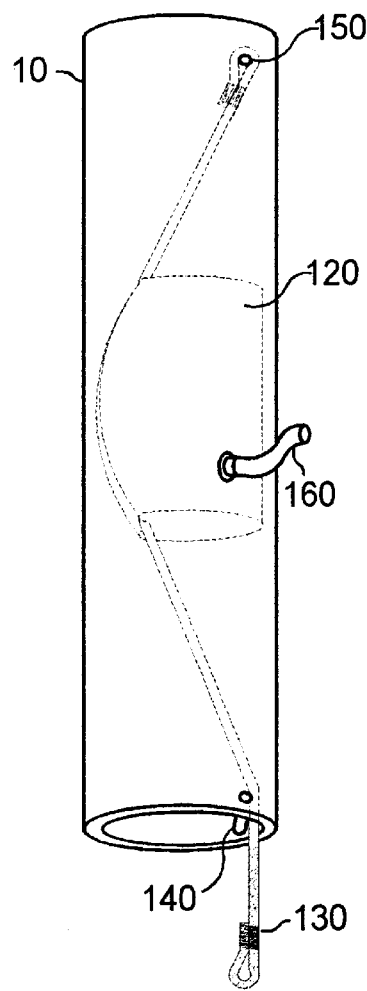

Artificial muscle 1000 is designed so that cable 130 passes from point of attachment 150 over bladder 120 and through low-friction cable-positioning means 140. When the bladder is deflated as shown in FIG. 1a, the cable runs in an nearly straight line over the deflated bladder, along said first side of the bone interior. The bladder may be inflated by externally connecting hose 160 to a source of pressurized fluid (such as compressed air), thus forcing the fluid into the bladder. When the bladder is inflated, as shown in FIG. 1b, it forces the portion of the cable passing over the bladder toward the opposing side of the bone interior. This pulls the cable in through the low-friction cable-positioning means. When it is desired to subsequently relax the artificial muscle, the fluid is allowed to leave bladder 120 through hose 160, by connecting hose 160 to an exterior low pressure sink (such as a vent to the atmosphere if the fluid is compressed air).

At first glance it might seem that the available force of the artificial muscle is basically independent of position. This is because the force pushing orthogonally on the tendon is approximately equal to the pressure of the fluid times the cross-sectional area of the bladder taken perpendicular to the force on the tendon; and neither the pressure or this area are much dependent on the muscle position. However, this perpendicular force on the cable is not the force of the muscle, which pulls in along the artificial tendon with a quite different force. The angle between the tendon and the bone wall near roller 140 is most acute when the bladder is deflated as in FIG. 1a; and this angle increases from this minimum throughout the range of motion up to full inflation as shown in FIG. 1b. By vector analysis, the tension or force pulling on the tendon is not just equal to the force pushing perpendicularly on the cable, but is also inversely proportional to the sine of this angle. Basically, the pulling force or tension on the tendon is strongly dependent on this mechanical advantage associated with this angle. So the available force is actually maximum when the muscle is at full extension, decreasing as the bladder inflates (and the sine increases). As desired, this approximates the force distribution of a biological muscle.

At this point, it is useful to discuss the geometrical limits on bone 10. The shape of the exoskeletal bone is not limited by the present invention to simple cylindrical pipes or other structural elements with uniform cross-sections. In fact, the exterior of said bone can be of essentially arbitrary shape, since it does not affect the functioning of the muscle analog. The interior surface, however, does affect the performance of the muscle analog.

It is clear from the discussion above that the bladder, when inflated, must push against the rigid interior surface of the bone whereto it is affixed and thereby exert force pushing the cable away from this surface. This works best if cable 120, when stretched tight between point of attachment 150 and roller 140, tends to run along the interior surface of the bone; this restricts the positioning of roller 140 and point of attachment 150.

This restriction on the placements of point of attachment 150 and roller 140 can be expressed most easily in terms of geodesics, where a geodesic is defined to be the shortest curve which can be drawn between two points on a surface. For example, on a spherical surface, geodesics are arcs drawn between the two points; on other surfaces, the geodesics are of differing shapes, depending on the curvatures of their surface. In the present invention, roller 140 defines a roller point on the interior surface of bone 10 near the center of said roller, and restricts cable 130 to pass near said roller point. If cable 130 were held tight between this point and point of attachment 150, it would run in a straight line in three-dimensional space, except where said interior surface interfered; the curve so defined is the shortest path that the cable can travel between said points within the bone, so that any deviation from this path (for example due to an inflated bladder exerting a transverse force on the cable) increases the length of cable between the two points. The roller point and point of attachment 150, also define a geodesic on the interior surface of said bone. According to a presently-preferred embodiment, roller 140 and point of attachment 150 should be placed so that cable 130, when held tightly between these points, should tend to pass along the interior surface of the bone, nearly tracing the geodesic connecting the points. On the interior of a cylindrical pipe such as that shown in FIGS. 1–3, this means that the geodesic should be nearly parallel to the axis of the pipe; the two points defining the geodesic should be on the same side of the pipe. Then a tensioned cable held between the two points would run in a straight line, alongside the geodesic. If instead the two points were on opposite sides of the pipe, the geodesic connecting them would be helical in shape; but the tightly-held cable would go in a straight line across the center of the pipe, nowhere near this geodesic. In this case, inflating a bladder wouldn't force the cable away from the interior surface as strongly if at all, since the cable doesn't tend to run along the interior surface, even when pulled tight.

Figures 2A, 2B, 2C:
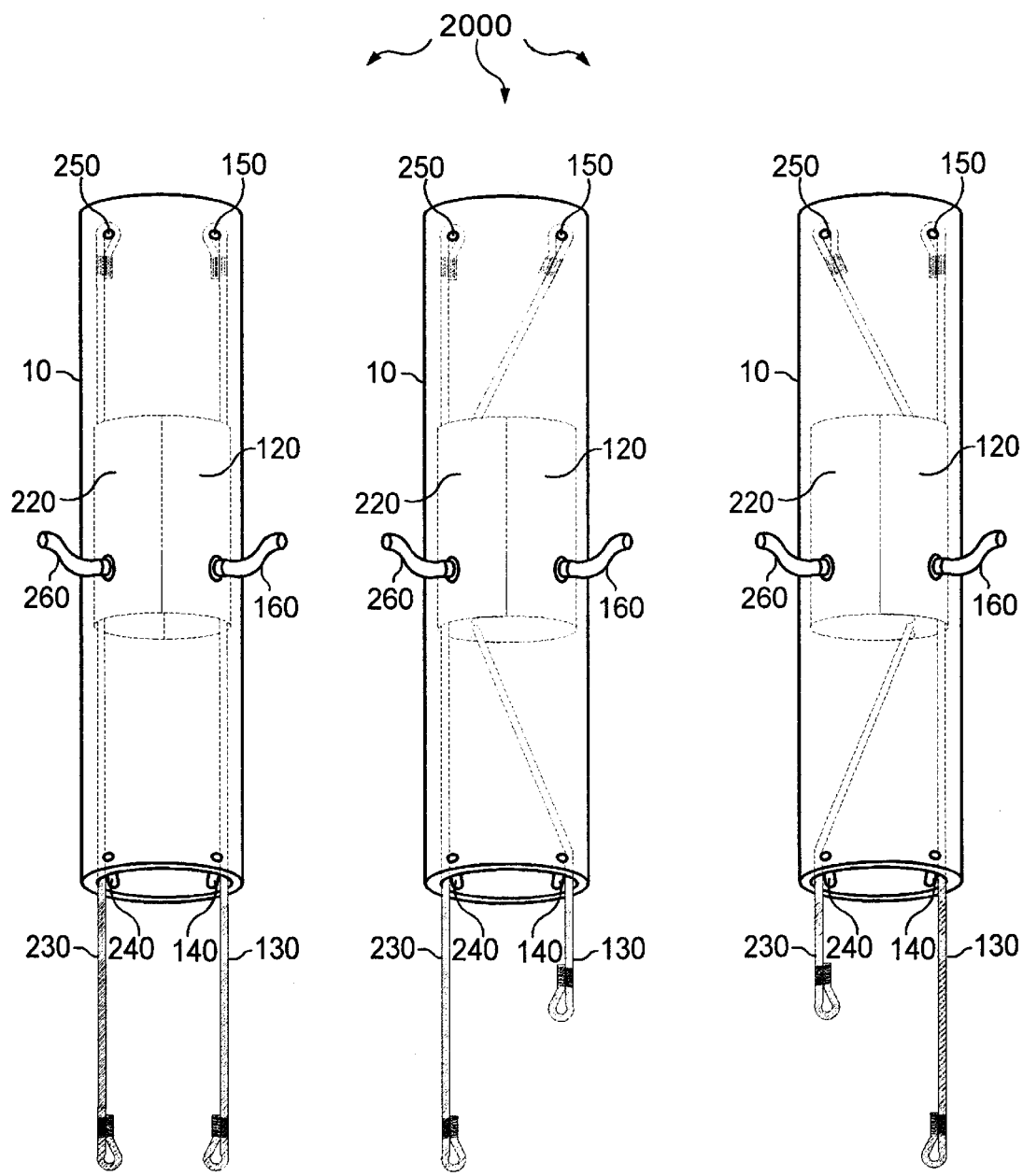

Description—FIG. 2a—Paired Opposing Artificial Muscles

Protein-based muscles only provide force in one direction—muscles shorten when stimulated by electrical nerve signals, thereby pulling on their respective tendons. Thus, in most biological motor systems, muscles are paired in opposition to allow a lever to be moved in either direction. For example, in a human arm, the biceps muscle pulls in its tendon in order to bend the arm, and the triceps muscle pulls in its tendon in order to straighten the arm. For motion to occur, the opposing muscle is generally relaxed as a given muscle is contracted. This paired arrangement is common to most organic systems, and a mechanical analog needs to be able to reproduce this effect FIG. 2a shows a paired opposing artificial muscle assembly 2000 which closely mimics this action. Assembly 2000 includes previously-described single artificial muscle assembly 1000 enclosed within bone 10, and further comprises a second bladder 220, cable 230, roller 240, point of attachment 250 and hose 260. Second cable 230 is affixed to the inside of bone 10 at second point of attachment 250 located on a second side of the interior of bone 10, directly opposing said first side. Roller 240 is affixed so as to constrain said second cable to move freely longitudinally along said second side of the bone interior. Second bladder 220 is affixed to said second side of the bone interior, directly opposing bladder 120. Cable 230 passes from point of attachment 250 over bladder 220 and through low-friction cable-positioning means 240. Second hose 260 provides the means for introducing and removing pressurized fluids to/from bladder 220; hose 260 may pass through the wall of the bone to connect with bladder 220 if desired, as shown for simplicity in FIGS. 2a,b,c. However, more in keeping with the endoskeletal theme of this design, hose 260 can alternatively be attached to the bladder inside bone 10, so that it may run inside the bone and be protected thereby.

Operation—FIGS. 2a,b,c—Paired Opposing Artificial Muscles

When a prior art double-acting pneumatic or hydraulic cylinder is used, one cylinder chamber is typically connected to the pressurized fluid source while the opposing cylinder chamber is simultaneously vented to an unpressurized fluid reservoir. This mode provides motion with the greatest speed and power possible for a particular configuration. The piston can be moved in either direction by selecting which chamber receives the pressurized fluid, and which chamber is vented. Unlike the force generated by the artificial muscles of the present invention, the force generated by a pneumatic cylinder in either direction is independent of the cylinder position; this force is determined only by the piston cross section and the fluid pressure.

Analogously, when inflating either bladder of double muscle assembly 2000, the opposing bladder is commonly vented to a low-pressure sink so that it may deflate freely. However, since the two bladders are mounted in physical opposition, the bladder which is inflating actually pushes against the bladder which is currently deflating, simultaneously helping to force any remaining fluid out of the bladder which is being exhausted. Thus, the contracting artificial muscle actually helps relax the opposing muscle, much like a double acting pneumatic or hydraulic cylinder.

Consider the arrangement shown in FIG. 2a. Tendons 130 and 230 both run between opposing bladders 120 and 220. In the most common and forceful type of motion, one bladder is inflated while the other bladder is simultaneously vented. For example, bladder 120 might be inflated through hose 160 while bladder 220 is vented through hose 260. With the artificial muscles arranged as shown in FIG. 2a, the air from vented bladder 220 is actually forced out under these conditions, because bladder 120 expands and pushes against bladder 220 as it inflates; the tensed artificial muscle actually "helps" the opposing muscle to relax. When bladder 120 is fully inflated and bladder 220 fully deflated, both cables are forced over to the second side of the pipe interior, as shown in FIG. 2b; this corresponds to the retracted position for cable 130 and the extended position for cable 230. Analogously, when bladder 220 is inflated through its hose 260 while bladder 120 is simultaneously vented, it forces both cables over to the first side of the pipe interior, as shown in FIG. 2c. This corresponds to the retracted position for cable 230 and the extended position for cable 130.

Two separate single muscle assemblies of the present invention, whose bladders are not mounted in physical opposition, do not enjoy this level of synergy. If two single muscle assemblies are used in this same manner, then only the tension induced on the tendon of the opposed relaxing muscle by the motion induced by the inflating muscle helps to deflate the bladder of the relaxed muscle. This causes the tendon of an artificial muscle to be tensed even while relaxing, rather than just when the muscle is itself tensed. In such a case, only the tendon pushes on the deflating bladder due to this induced tension, rather than the uniform pressure of the opposing bladder inherent in the opposed assembly depicted in FIGS. 2a,b,c.

Description—FIGS. 3a,b—Robotic Arm Powered by Paired Opposing Artificial Muscles FIGS. 3a,b show a robotic arm 3000 of the present invention, including and powered by paired opposing artificial muscle assembly 2000. Referring to FIG. 3a, robotic arm 3000 comprises a bone 10 which forms the upper arm and also contains muscle assembly 2000. Arm 3000 further comprises a joint, axle, or pivot 20, a forearm 30 and attachment points 40,42 located on forearm 30 where the free ends of tendons 130,230 are affixed, respectively. As a simple means of allowing forearm 30 a limited range of motion when rotating around the axis of pivot 20, the end of bone 10 nearest rollers 140 and 240 has now been cut diagonally.

In robotic arm 3000, the upper arm is formed by bone 10. In fact, the bladders 120,220 of the opposing artificial muscles are located at approximately the equivalent positions taken by the biceps and triceps muscles, respectively, in a human upper arm. Pivot 20 forms the elbow joint of the arm. Forearm 30 is connected to bone 10 by pivot 20, and when the artificial muscles are both relaxed, can rotate freely around this pivot point between limits dictated by the diagonal cut at the end of bone 10. The free ends of cables 130,230 are affixed to forearm 30 at attachment points 40 and 42, respectively. This arrangement mimics a human arm; when driven appropriately by artificial muscle assembly 2000, the robotic arm may be extended or bent as desired.

Operation—FIGS. 3a,b—Robotic Arm Powered by Paired Opposing Artificial Muscles FIG. 3a shows robotic arm 3000 in the fully bent position, with forearm 30 resting against the upper edge of the diagonal end of bone 10. Paired artificial muscle assembly 2000 is in the state shown in FIG. 2b, with bladder 120 inflated and bladder 220 deflated. In this state, both cables are forced over to the second side of the bone interior, so that cable 130 is retracted and cable 230 is extended. With the offset location of attachment points 40,42, this forces forearm 30 to rotate counterclockwise to its "bent" stop at the upper edge of the diagonal bone end.

FIG. 3b shows robotic arm 3000 in its fully extended position, with forearm 30 resting against the lower edge of the diagonal end of bone 10. Paired artificial muscle assembly 2000 is in the state shown in FIG. 2c, with bladder 220 inflated and bladder 120 deflated. In this state, both cables are forced over to the first side of the bone interior, so that cable 230 is retracted and cable 130 is extended. With the offset location of attachment points 40,42, this forces forearm 30 to rotate clockwise to its "extended" stop at the lower edge of the diagonal bone end.

Figure 4A:
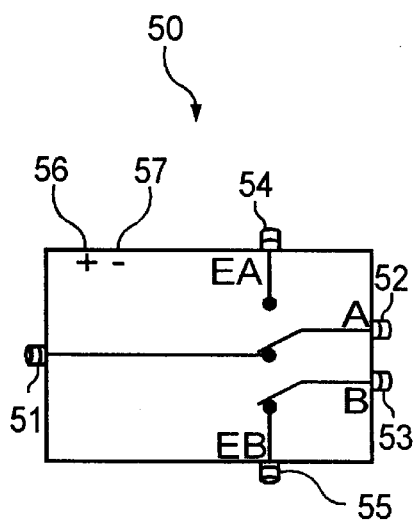
FIG. 4d is a diagram showing how valve 50a might be connected to control robotic arm 3000.
FIG. 4e is a diagram showing the symbol used to represent prior-art 2-port, 2-position valve 60.

Description—FIGS. 4a,b—Coarse Control of Paired Opposing Artificial Muscles

When a prior-art double acting pneumatic cylinder is used, one cylinder chamber is typically connected to a source of compressed air while the opposing cylinder chamber is simultaneously vented to an unpressurized fluid reservoir. This allows the piston to move in either direction by forcing the air into one chamber while simultaneously forcing the air out of the opposing chamber. The fluid flow is controlled through the opening and closing of valves, typically electrically-controlled solenoid valves. Such valves operate by connecting fluid ports together in various combinations; the user selects the desired combination by selectively energizing the solenoid (or not), which either extends or retracts the ferrous solenoid core. This solenoid core is physically linked to hardware which selectively connects the ports together according to a predetermined plan, as a result of this movement of the solenoid core FIG. 4a shows a schematic representation of a prior-art 5-port 2-position solenoid valve 50 of a type commonly used to control a double acting pneumatic cylinder. In valve 50, compressed air may be introduced through a first pressure port 51. Two more ports, typically labeled A and B, are intended for connection to the two opposing chambers of a double acting pneumatic cylinder; here these are labeled as ports 52 and 53, respectively. Two final ports, commonly labeled EA and EB (short for Exhaust A and Exhaust B) are generally open to atmospheric pressure. However, flow-control means (such as a constriction limiting the size of the opening) may be connected between these ports and the atmosphere if it is desired to limit the rate at which a chamber can be exhausted, thus limiting the speed at which the cylinder can move. Exhaust ports EA and EB are labeled 54 and 55, respectively, in FIG. 4a. The solenoid valve is controlled by either applying approximately 0V (to leave the valve in its initial or resting state) or a predetermined voltage (to energize the solenoid and switch it to an alternate state) across terminals 56 and 57. Although a particular polarity is associated with terminals 56,57, solenoid valves usually respond identically to signals of either polarity (the coil still pulls in the ferrous solenoid core regardless of which way the current flows). Moreover, if a particular valve does happen to be polarity dependent, the circuitry discussed herein can easily be modified to rectify the appropriate signals by one of average skill in the art. Therefore, for simplicity it is assumed that all solenoid valves shown hereinafter are polarity independent.

As shown in FIG. 4a, valve 50 at rest (no voltage applied to terminals 56,57) connects pressure port 51 to A (port 52), and connects B (port 53) to EB (port 55). When the solenoid is energized (by applying the correct voltage across terminals 56,57), valve 50 connects pressure port 51 to B (port 53), and connects A (port 52) to EA (port 54). Thus, by connecting port 51 to a source of compressed air, connecting hoses from ports 52,53 to the first and second opposing chambers of a double acting pneumatic cylinder, respectively, and leaving ports 54,55 open to the atmosphere, the cylinder can be controlled. With the valve at rest, the first chamber will thus be pressurized, with the second chamber vented to the atmosphere, and with the valve energized, the second chamber will be pressurized, with the first chamber vented to the atmosphere. If the cylinder's motion is not opposed with an equal or greater force, the cylinder will move to its furthest extent in one direction when the valve is at rest, and will move to its furthest extent in the opposite direction when the valve is energized.

As discussed previously, paired artificial muscle assembly 2000 functions somewhat like a double acting pneumatic cylinder, and if properly mounted can replace a double acting pneumatic cylinder in most applications. Not surprisingly, assembly 2000 can also be controlled using valve 50, in a manner analogous to the control method just described for the double acting pneumatic cylinder.

Figure 4B:
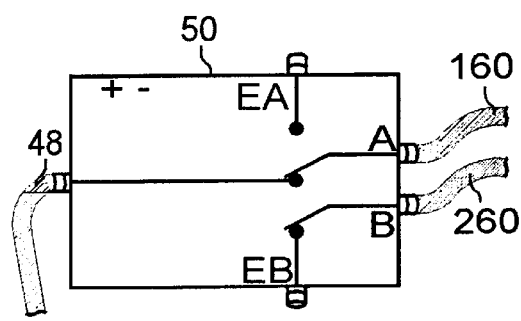

Now consider how robotic arm 3000, including and powered by paired artificial muscle assembly 2000, might be controlled using valve 50. Referring to FIG. 4b, a connection scheme can be seen whereby valve 50 may be used to control arm 3000. First, ports 52,53 should be connected to hoses 160 and 260, respectively. Port 51 is connected to a source of compressed air through a hose 48. For simplicity, exhaust ports 54,55 are merely left open to the atmosphere.

Operation—FIGS. 3ab,4bcd—Coarse Control of Paired Opposing Artificial Muscles

Referring again to FIGS. 4b and 3ab, we can see how this control system works. With valve 50 de-energized, bladder 120 is connected to the source of compressed air through hose 160, valve 50, and hose 48. Bladder 120 will thus be inflated until its pressure equalizes with the compressed air source. At the same time, bladder 220 is vented to the atmosphere through hose 260, valve 50, and exhaust port 55. If the force thus generated is not opposed by a greater force, this will eventually result in bladder 120 becoming fully inflated and bladder 220 becoming fully deflated, arm 3000 will thus move to the "bent-arm" state depicted in FIG. 3a. If arm 3000 was located in a different position prior to valve 50 being de-energized, it will move from its starting position to this bent-arm state as bladder 120 inflates.

Analogously, with valve 50 energized, bladder 220 will be pressurized, with bladder 120 vented to the atmosphere and eventually deflated. If not opposed by an equal or greater force, this eventually will result in arm 3000 assuming the "extended-arm" state depicted in FIG. 3b. If arm 3000 was located in a different position prior to valve 50 being energized, it will move from its starting position to the extended-arm position as bladder 120 inflates.

With a control system based entirely on valve 50, there is no way to controllably stop the motion of arm 3000 at any position except by crudely opposing it with a matching force or letting the forearm run into one of the limits of its range of motion. Thus, this coarse control system is best thought of as an "arm-in-motion" control system; its mere two possible states result in maximum-strength motion in opposite directions, stopping only when the arm runs into a limit or when it encounters a large enough opposing force. Some speed control of the arm's motion may be attained as with the pneumatic cylinder, by introducing flow-control means between the exhaust ports and the atmosphere; this limits the rate at which a previously-inflated bladder can be deflated, which also limits the rate at which the opposing bladder can be inflated. But true controllable positioning of arm 3000 is not attainable based solely on valve 50.

Figure 4C:
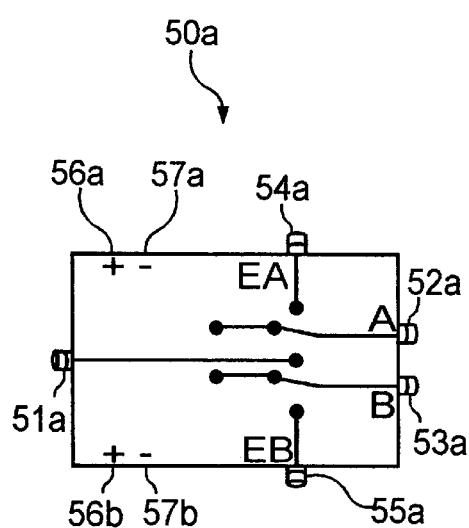

One alternate type of commonly-available valve can be used to provide a somewhat greater flexibility of control; this is the 5-port, 3-position solenoid valve 50a with a locking position, shown in FIG. 4c, which is closely related to valve 50 Valve 50a has the same two states as valve 50, as well as an additional third state wherein all the ports are isolated from one another; typically, this type of valve has two solenoids, represented in FIG. 4c by two pairs of electrical terminals 56a,57a and 56b,57b. As shown in FIG. 4c, valve 50a at rest (no voltage applied to terminals 56a,57a or 56b,57b) isolates all ports from each other. When the first solenoid is energized (by applying the correct voltage across terminals 56a,57a) valve 50a connects pressure port 51a to B (port 53a), and connects A (port 52a) to EA (port 54a). When the second solenoid is energized (by applying the correct voltage across terminals 56b,57b), valve 50a connects pressure port 51a to A (port 52a), and connects B (port 53a) to EB (port 55a).

Thus, by connecting a source of compressed air to port 51a, connecting hoses from ports 52a,53a to the first and second opposing chambers of a double acting pneumatic cylinder, respectively, and leaving ports 54a,55a open to the atmosphere, the cylinder can be controlled. With the second solenoid of valve 50a energized, the first chamber will thus be pressurized, with the second chamber vented to the atmosphere; and with the first solenoid of valve 50a energized, the second chamber will be pressurized, with the first chamber vented to the atmosphere. If the cylinder's motion is not opposed by an equal or greater force, the cylinder will move to its furthest extent in one direction when the first solenoid is energized, and will move to its furthest extent in the opposite direction when the second solenoid is energized. With the valve at rest, both chambers will be isolated and the cylinder will settle in a position where any external forces balance with the pressures in the chambers.

Three-position valves such as valve 50a are most commonly used to control double acting hydraulic cylinders, where the new third state represents a true "locked cylinder" state; with the valve "locked" and all ports isolated, the hydraulic cylinder will be held in place by essentially-incompressible hydraulic fluid trapped in both cylinder chambers. Because the hydraulic fluid is essentially incompressible, its pressure can change from a very high value to near zero pressure with essentially no compensating movement of the piston; so when the valve enters the isolated state, the hydraulic cylinder will stop immediately and be locked in place. When a valve 50*a* is used to control such a hydraulic cylinder, the exhaust ports EA and EB are typically connected through hoses to an unpressurized hydraulic fluid reservoir; and the hydraulic pump providing pressurized fluid has its intake in this reservoir.

However, with a pneumatic cylinder, this third isolated valve state does not truly represent a locked-cylinder state. For a pneumatic cylinder controlled using valve 50*a*, only one cylinder chamber is pressurized when entering this "locked" state; in moving to the locked position, one chamber is always pressurized and the other is presumably vented to atmosphere. So when valve 50*a* is moved to its third, isolated state, the cylinder has one chamber pressurized near the pressure of the compressed air source, and the other nearer atmospheric pressure. If the cylinder is not up against a limit of motion when the valve is placed in the isolated state, the cylinder will continue to move until the opposing pressures in the two chambers equalize with any externally-applied forces.

Figure 4D:
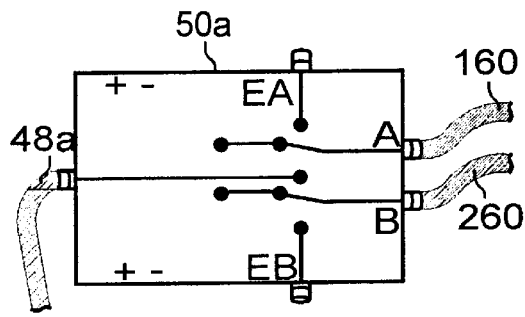

A similar situation exists if valve 50*a* with its built-in locking position is used to control robotic arm 3000. Referring to FIG. 4*d*, a connection scheme can be seen whereby valve 50*a* may be used to control arm 3000 First, ports 52*a*,53*a* should be connected to hoses 160 and 260, respectively. Port 51*a* is connected to a source of compressed air through a hose 48*a*. For simplicity, exhaust ports 54*a*,55*a* are merely left open to the atmosphere. With the second solenoid of valve 50*a* energized, bladder 120 is connected to the source of compressed air through hose 160, valve 50*a*, and hose 48*a*. Bladder 120 will thus be inflated until its pressure equalizes with the compressed air source. At the same time, bladder 220 is vented to the atmosphere through hose 260, valve 50*a*, and exhaust port 55*a*. If the force thus generated is not opposed by a greater force, this will eventually result in bladder 120 becoming fully inflated and bladder 220 becoming fully deflated; arm 3000 will move to the "bent-arm" state depicted in FIG. 3*a*. If arm 3000 was located in a different position prior to the first solenoid of valve 50*a* being energized, it will move from its starting position to this bent-arm state as bladder 120 inflates.

Analogously, with the first solenoid of valve 50*a* energized, bladder 220 will be pressurized, with bladder 120 vented to the atmosphere and eventually deflated. If not opposed by a greater force, this eventually will result in arm 3000 assuming the "extended-arm" state depicted in FIG. 3*b* If arm 3000 was located in a different position prior to the second solenoid of valve 50*a* being energized, it will move from its starting position to the extended-arm position as bladder 120 inflates.

When valve 50*a* is de-energized, all ports of valve 50*a* are isolated. Now consider what happens if valve 50*a* is shifted to its third "isolated" state while the arm is in motion, powered by paired artificial muscle assembly 2000. The air in one bladder is pressurized, while the other, having recently been vented to the atmosphere, is nearer atmospheric pressure. Thus, the arm will continue moving in the same direction until the pressures in the two bladders equalize in a position where the forces exerted on tendons 120 and 220 may also equalize with any externally-applied forces.

Clearly, a valve such as valve 50*a* is not an adequate solution for controlling robotic arm 3000 if accurately controllable positioning or stops at intermediate positions are desired; there is an undesirable "lag" both in time and position between when the valve is isolated and when the arm actually stops moving. This is an inherent problem caused by the compressibility of the fluid used. In fact, valve 50*a* is not even an adequate solution for cylinders using any compressible fluid, such as pneumatic cylinders. Neither this control system or the arm-in-motion coarse control system using only valve 50 described above is sufficient to adequately mimic the biological motion of an arm driven by opposing muscle groups.

Interestingly, if the fluid used in the artificial muscles was essentially incompressible, then arm 3000 would stop immediately when valve 50*a* entered its isolated state. Thus, a control system using only valve 50*a* would be sufficient to accurately control arm 3000 if the artificial muscles used an essentially incompressible fluid. In fact, paired artificial muscle assembly 2000 would act much like a hydraulic cylinder if incompressible fluid was used. And the motion would likely be even more powerful than a pneumatic arm in such a case.

However, the motion produced by such a "hydraulic arm" would match biological motions less well; some "natural" modes of movement are difficult to mimic with a hydraulic system. For example, the truly locking nature of a hydraulic arm is not matched in nature. And the motion of an hydraulic arm would probably be quite slow compared to biological motion due to the relative viscosity of hydraulic fluids. Further, materials strong enough to withstand common hydraulic system pressures are not as flexible as would be desired to perform well as bladders. Finally, the weight of the hydraulic fluid adds to the overall weight of the design Nevertheless, it is worthwhile to realize that an artificial muscle of the present invention based on incompressible fluids is also possible, and that an accurate and simple positioning system for an hydraulic arm 3000 can be based entirely on a single valve 50*a*. Such an arm might have advantages in some applications.

Description—FIG. 4*b*—Desirable Refinements for Improved Control of Paired Opposing Artificial Muscles and Required Hardware Opposed pairs of organic muscles are controllable in much more complicated patterns than the simplistic pneumatic and hydraulic control systems described above. Again using the example of a human arm controlled by the opposing biceps and triceps muscle groups, the main "modes of operation" of an organic muscle pair can be described.

1) First of all, it is possible to actuate the biceps muscles to bend the arm to a desired position, while leaving the triceps muscle relaxed. For example, when bending the arm against an opposing force, such as when a weightlifter "curls" a barbell (standing upright with the upper arms unmoving and lifting the barbell against gravity using only the biceps), the triceps is left relaxed at all times; only the biceps exerts force. Even if the load changes, only the force exerted by the biceps need change in order to compensate for the changed resistance. If additional weight is added to or removed from the weightlifter's barbell, the barbell may accelerate momentarily, even backward, until he senses the changed weight and adjusts his force. However, since the expected load is supported completely by the biceps, the triceps muscle is left relaxed throughout. And as long as the weight is not beyond his strength, the weightlifter can continue curling the barbell until the motion is completed. This is the primary mode used for actually bending the arm, especially if moving a load; since the active biceps is opposed by a relaxed triceps, this mode gives the maximum available force. This mode is not truly supported by the arm-in-motion coarse control system described above, since that system provides no way to stop the arm once it reaches a desired location.

2) In the opposite analogous case, as when the weightlifter is doing reverse curls (bending over with the upper arm held unmoving and lifting the barbell against gravity using only the triceps), only the triceps is "enabled"—the biceps muscle is left relaxed regardless of the load placed on the triceps muscle. Again, this is the primary mode used for actually straightening the arm to a desired position, perhaps resisting a load; since the active triceps is opposed by a relaxed biceps, this mode gives the maximum available force. This mode is also not truly supported by the arm-in-motion coarse control system described above, based on valve 50 alone When using either of these two first modes to move the arm while opposing a load, it is possible for a biological muscle system to increase the exerted force from the actuated muscle, while leaving the opposed muscle relaxed. As mentioned above, if additional weight is added to the barbell, a weightlifter can compensate by increasing the exerted force as long as the weight is not increased beyond his ability.

Also, when opposing a load, it is possible for the biological muscle system to decrease the exerted force from the actuated muscle, again while leaving the opposed muscle relaxed. For example, when the weightlifter finishes his motion, he can controllably decrease his force in order to allow the barbell to slowly move back to its original position. This mode is not supported at all by the arm-in-motion coarse control system described above; with that system, the force in the actuated direction can only increase, never decrease. If valve 50 is switched to the opposite state, the force does decrease as the bladder is vented; but the opposing bladder simultaneously becomes pressurized, actually forcing the arm in the opposite direction rather than just reducing the force opposing this motion. The coarse control system described above cannot mimic this biological motion of controllably "letting down" a load.

Because of the provision for moving to a "desired position", these control modes require a feedback loop of some sort in order to mimic the human ability to sense deviations from the desired location and increase or decrease the exerted force to return to the desired position. The coarse control system described previously has no means of copying these modes. Even if a feedback loop of some type were realized, the best "hold" that would be attainable using only valve 50 would move the arm to the desire location and then make valve 50 switch back and forth between its two states, oscillating the arm around the desired location, wasting power and compressed air.

Of course, if valve 50a with its third locking position was used rather than valve 50, and assuming that a feedback system were present, then the arm could be "locked" when it reached the desired position by putting the valve in its third isolated state. However, even this arrangement is not optimal for these modes, because the opposing muscle does not remain relaxed. For example, if the arm approaches the desired position but overshoots, it would not be locked in place because of the deviation due to the overshoot. But with this arrangement, the valve cannot just release a little air from the activated muscle and "ease back" to the right position. Instead, when the excess air is released from the pressurized bladder, the arm is simultaneously "forced" back as the opposing bladder is pressurized. This is likely to cause an overshoot in the opposite direction. So if arm 3000 is controlled with a feedback loop, even using valve 50a, the arm is likely to oscillate a few times before finally settling close enough to the desired position so that the valve can be finally locked.

Basically, both of these two first modes require a control system which: 1) allows one muscle to be controllably enabled while the opposing muscle is completely disabled; and 2) makes provision for a "target" position to be assigned. For example, with such a control system the arm can "curl" a weight by setting a target position at the fully-bent position, with the biceps enabled and triceps relaxed.

When the curling motion is completed, the target position can be reset to the fully-extended position, with the biceps still enabled and the triceps still relaxed so that the biceps relaxes and lets the weight down. And if the let-down motion is too abrupt when done in one step, the target position can be moved slowly back to the fully-extended position, perhaps in a series of steps, so that the weight is let down controllably.

3) Thirdly, it is possible for an arm to be held in a desired position against perturbing forces in either direction of any manageable magnitude. Once in any chosen position, the arm may be held in place by sensing any deviations from the desired location and opposing these motions with whatever increased or decreased force is necessary to return the arm to the desired position. This mode is distinct from the first two modes in that it requires both muscles to be enabled so that force may be exerted in either direction. For example, if someone desires to hold his arm at an intermediate position, he can do so, regardless of any increases or decreases in force pushing the arm in either direction (as long as it does not exceed his ability). He can do this by controllably increasing the force exerted by his biceps muscle and simultaneously decreasing the force exerted by his triceps in order to oppose a perceived "straightening force", and he can do this by controllably increasing the force exerted by his triceps muscle and simultaneously decreasing the force exerted by his biceps in order to oppose a perceived "bending force". Both muscles are enabled for this mode.

4) Also, in a human arm it is possible to isometrically oppose the forces exerted by the biceps and triceps muscles against each other by "tensing" the arm, essentially locking the arm in a desired position. This is similar to the "locking" mechanisms discussed for hydraulic and pneumatic cylinders. Although this mode is inefficient and tiring for biological muscle systems, it requires little or no energy and can be useful for the artificial muscle systems of the present invention. With the arm-in-motion coarse control system, even with a feedback loop, the closest approach to this would be the "oscillating arm" state described above, there is no way to lock the arm with the coarse control system.

5) Finally, it is possible to fully relax a human arm so that it "flops" or goes to whatever position is imposed by external forces. Although this is not a particularly useful mode, it is possible and may be useful in setting a known starting point for further motions.

Thus, in order to provide an artificial muscle system which approaches biological muscle behavior, an improved control system is required, able to mimic these control modes; valve 50 alone is not sufficient to achieve this level of control. Even valve 50a with its inherent locking position is not able to achieve this level of control unless incompressible fluids are used; and even then, a "hydraulic" arm acts differently than a biological arm. The improved pneumatic control system of the present invention requires the addition of several new elements, including additional valves and electrical circuitry.

According to a presently-preferred embodiment, the improved control system is constructed from readily available prior art components. For example, the 5-port, 2-position pneumatic valve 50 is still used, because of its widespread availability and familiarity in applications controlling double acting pneumatic cylinders in analogous applications. In addition, two simple on-off valves with separate controls are used in order to better control the muscle analogs. Those of ordinary skill in the art will see that these three valves might well be combined into a single solenoid-controlled pneumatic valve assembly with equivalent overall functionality. However, if such an assembly is currently manufactured, it is not widely available at this time; and the design of such a combined valve assembly is beyond the scope of the present invention. Therefore the construction of the improved control system from readily available prior art components is not to be taken as limiting but only as illustrative of the techniques involved.

Figure 4E:
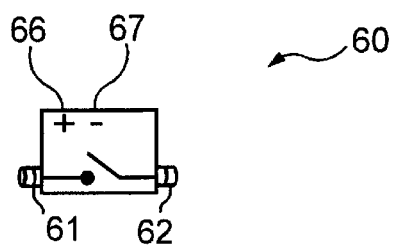

FIG. 4e shows the symbol used hereinafter for one of the additional components used in the improved control system: a simple "on-off" pneumatic switch, prior-art 2-port 2-position pneumatic valve 60. As with valve 50, valve 60 includes a solenoid and is electrically controlled. Pressure port 61 is connected to port 62 only when the appropriate voltage is applied to terminals 66,67. When no voltage is present at these terminals, port 62 is isolated from port 61.

Description—FIGS. 5ab,6a,7—Circuit Blocks Used in Improved Control System for Opposing Artificial Muscles FIG. 5a is a schematic circuit diagram of a familiar prior-art bipolar push-pull subcircuit 70, commonly seen in amplifying circuits. As shown in the figure, two opposing bipolar transistors, NPN transistor 71 and PNP transistor 72, are connected in series with the emitters connected together at common-emitter output terminal 73. The collectors 74,75 of transistors 71,72 are typically connected to positive and negative power supplies, respectively. The base terminals 76,77 of transistors 71,72, respectively, are used to control the transistors and thus stage 70. A load resistor 78 is connected between common-emitter terminal 73 and a reference terminal 79, which commonly is grounded.

FIG. 5b is a schematic diagram of a typical prior-art arrangement of stage 70, commonly known as a class B output stage. In this configuration, a common input voltage Vi is connected to the bases 76,77 of both transistors; the collectors 74,75 are connected to symmetric positive and negative power supplies +Vcc and −Vcc, respectively; and reference terminal 79 is grounded. The output voltage Vo is measured at terminal 73.

FIG. 6a is a schematic circuit diagram of a modified version of the class B output stage; here an additional pair of diodes, connected with the same polarity as the emitter-base junctions of the transistors, is connected in series between the emitters of the two transistors.

FIG. 7 is a schematic diagram of a valve-control circuit 80 which is also based on push-pull subcircuit 70. In circuit 80, a bias resistor 81a is connected between the positive power supply +Vcc and base terminal 76 of the NPN transistor; a second identical bias resistor 81b is connected between the negative power supply −Vcc and base terminal 77 of the PNP transistor. Two identical bias diodes 82a,b are connected in series between base terminals 76 and 77, paralleling the emitter-base junctions of both transistors, and having the same polarity, node 83 forms the connection point between the two diodes. Thus, the anode of first diode 82a is connected to terminal 76 and its cathode is connected to node 83; and the anode of second diode 82b is connected to node 83 with its cathode connected to terminal 77. An input control terminal 85 is connected by an input resistor 84 to node 83. In circuit 80, the reference terminal 79 within subcircuit 70 is again grounded, but in this case the value of resistor 78 is set to 0 ohms. Collector 74 of the NPN transistor is connected to the cathode of a diode 86; the anode of this diode is connected to an output terminal 88. Collector 75 of the PNP transistor is connected to the anode of another diode 87; the cathode of this diode is also connected to output terminal 88.

Operation—FIGS. 5abc,6ab,7—Circuit Blocks Used in Improved Control System for Opposing Artificial Muscles As typically used, subcircuit 70 of FIG. 5a has a voltage gain of approximately one, but has a large current gain; it is usually seen where these characteristics are required. Usually, the collectors 74,75 of the NPN, PNP transistors are connected to positive and negative power supplies, respectively. Users of this circuit block ensure that the bases of the two transistors are never biased such that both transistors are on at the same time, since this would create a direct path from the positive power supply to the negative supply, damaging the transistors. This common circuit block is used several times in the improved control system of the present invention.

In the particular configuration of subcircuit 70 seen in FIG. 5b, the two base terminals 76,77 are connected together and controlled by the same input voltage Vi; this ensures that both transistors cannot be enabled at the same time. Each of the two transistors acts as an emitter follower for input voltages Vi of the appropriate polarity. Essentially, NPN transistor 71 is active when Vi is greater than the reference voltage at reference terminal 79, in this case 0V, with transistor 72 shut off. And PNP transistor 72 is active when Vi is less than 0V, with transistor 71 shut off.

FIG. 5c shows an approximate transfer characteristic expected of the circuit depicted in FIG. 5b. Since each transistor acts as an emitter follower, the output voltage will be approximately equal to the input voltage offset by the voltage drop across a diode, in each direction. For example, if one assumes a first-order diode drop of 0.7V, then for −Vcc<Vi<−0.7V, the output voltage Vo is approximately equal to (Vi+0.7). For −0.7<Vi<0.7, Vo is about 0V (this approximation is only to first order and will be discussed further below). For 0.7<Vi<Vcc, Vo is approximately equal to (Vi−0.7V). As Vi increases toward +Vcc, Vo eventually is limited to Vcc−Vce(on) when transistor 71 saturates; however, Vce(on) can be very near zero (typically less than 0.2V). Similarly, as Vi decreases toward −Vcc, Vo eventually is limited to −Vcc+Vce(on) when transistor 72 saturates; however, Vce(on) can be very near zero (typically less than 0.2V).

The transfer characteristic shown in FIG. 5c is centered around the origin only because reference terminal 79 is grounded in FIG. 5b. If reference terminal 79 were instead held at some other voltage Vref, where Vref is within the power supply range (−Vcc<Vref<Vcc), the transfer characteristic would be quite similar, except it would be shifted to center around (Vi,Vo)=(Vref,0 v) rather than (0 v,0 v).

The characteristic "flat spot" near the origin of the transfer characteristic of FIG. 5c gives rise to the familiar crossover distortion associated with Class B output circuits such as that shown in FIG. 5b. It is a goal of the present invention to use this circuit in a new way in order to take advantage of this flat spot in providing an electric-pneumatic feedback loop with controlled sensitivity.

The circuit shown in FIG. 6a is closely akin to the class B output circuit of FIG. 5b. This circuit has the modified transfer characteristic shown approximately in FIG. 6b, with an even larger "flat spot" in the transfer characteristic than was seen in FIG. 5c. The flat spot is approximately twice as large as that seen in FIG. 5c. The analysis of FIG. 5b still holds in terms of each transistor acting as a voltage follower for voltages of the correct polarity, but now there is an additional diode drop in each direction from one of the two new symmetrically-placed diodes introduced into the circuit. This circuit is shown as an option to be used if such a larger "flat-spot" is desired than is provided by the circuit of FIG. 5a in the control circuitry of the present invention. Those of average skill in the art will see that this technique may be used with any number of diodes (an even integer if a symmetric transfer characteristic is desired) if an even-larger flat spot is desired.

Circuit 80 shown in FIG. 7 is another modified form of push-pull circuit 70. The most striking feature of this configuration of subcircuit 70 is that neither transistor collector 76,77 is connected to a power supply. This is because voltages between −Vcc and +Vcc are applied through a solenoid winding to terminal 88 of circuit 80 in operation, and circuit 80 is used to control the completion of this current path to ground. Diodes 86 and 87 are present to protect the collector-base junctions of transistors 71 and 72 from becoming forward-biased and passing significant current when the voltage on terminal 88 varies.

The improved control system of the present invention provides a primary control signal which when activated approximates either −Vcc or +Vcc, and which is connected to the positive terminal of each solenoid valve. As previously mentioned, solenoid valves are typically polarity independent; so if the negative terminal of a solenoid valve is simply grounded, then that valve will be energized whenever this primary control signal goes to either +Vcc or −Vcc. Using circuit 80, however, the energizing current may be controllably enabled as a function of a secondary control signal (the signal at terminal 85 of circuit 80).

When using circuit 80 of FIG. 7, terminal 88 is connected to the negative terminal of the solenoid valve. Then, if the valve's positive terminal goes to +Vcc, this voltage appears at terminal 88 through the coil winding. Since this voltage is greater than ground, the only available current path is through diode 86 and transistor 71 to ground; and this path is only enabled when transistor 71 is on. If input terminal 85 is held at ground potential or above, the base-emitter junction of transistor 71 will be forward biased, and transistor 71 will be enabled. Current will flow and increase until transistor 71 saturates (with terminal 88 at approximately 0.9V); the solenoid valve will be energized (this valve is chosen so that it can operate with a voltage of Vcc−0.9V). If the voltage at control terminal 85 is lower than ground, transistor 71 will be cut off and the valve will not be energized when the valve's positive terminal goes to −Vcc.

Similarly, if the valve's positive terminal goes to −Vcc, this voltage appears at terminal 88 through the coil winding. Since this voltage is less than ground, the only available current path is through diode 87 and transistor 72 to ground; and this path is only enabled when transistor 72 is on. So if input terminal 85 is held at ground potential or below, the base-emitter junction of transistor 72 will be forward biased, and transistor 72 will be enabled. Current will flow and increase until transistor 72 saturates (with terminal 88 at approximately −0.9V); the solenoid valve will be energized (this valve is chosen so that it can operate with a voltage of Vcc−0.9V). If the voltage at control terminal 85 is higher than ground, transistor 72 will be cut off and the valve will not be energized when the valve's positive terminal goes to −Vcc.

If input terminal 85 is held exactly at ground, or if it is allowed to float so that node 83 goes to ground, then the base-emitter junctions of both transistors are biased on so that both transistors are enabled for the appropriate voltage conditions. Circuit 80 is enabled for voltages at terminal 88 of either +Vcc or −Vcc. If the valve's positive terminal goes to +Vcc, the current path is through diode 86 and transistor 71 to ground is enabled; and if the valve's positive terminal goes to −Vcc, the current path through diode 87 and transistor 72 to ground is enabled. So one can see that circuit 80 of FIG. 7 functions to provide an effective ground connection to the negative terminal of a solenoid valve for voltages at the positive terminal of the solenoid valve of: 1) only +Vcc if terminal 85 is held high (above ground); 2) only −Vcc if terminal 85 is held low (below ground); and 3) either +Vcc or −Vcc if terminal 85 is grounded or floating.

Description—FIGS. 8,9abc—Improved Control Systems for Opposing Artificial Muscles FIG. 8 is an exploded view of pivot assembly 20 of robotic arm 3000. In the improved control system of the present invention, a potentiometer 22 linked to the rotation of the elbow joint is used as a means of measuring the position of the robotic arm. A commonly-available type of potentiometer with a cylindrical encased body 22b and a protruding slotted stem 22s is shown in FIG. 8. Although it is not particularly important exactly what type of potentiometer is used or how it is physically mounted (as long as it turns when the elbow joint turns), FIG. 8 shows one presently-preferred method of mounting the potentiometer.

In FIG. 8, a proposed pivot assembly 20 is shown. In keeping with the theme of providing protection to fragile components within robust structural members, the pivot assembly is based around a rigid, strong tubular pivot shell or pipe 24, which contains and protects potentiometer 22. The body of potentiometer 22 rotates in unison with pivot shell 24, since key 22k located on the body 22b of potentiometer 22 mates with keyway 23 in the interior of pivot shell 24. Pivot shell 24 fits through bearing assemblies 26 and 28, which are mounted within and affixed to bone 10. After arm 3000 is assembled, pivot shell 24 is solidly attached to forearm 30 so that the body 22b of potentiometer 22, pivot shell 24 and forearm 30 all rotate in unison around the pivot axis as robotic arm 3000 is extended or bent. L-shaped member 21 is mounted fixedly on the exterior of bone 10, with the screwdriver-headed end extending into the end of pivot shell 24 and mating with the slotted stem 22s of potentiometer 22. Thus, as arm 3000 rotates through its allowed range of motion, the stem 22s of potentiometer 22 rotates with respect to the body 22b of the potentiometer. The electrical connections of potentiometer 22 are discussed in the descriptions of FIG. 9 below.

FIG. 9a is a schematic diagram of a first embodiment 100a of the novel control system of the present invention, intended for use with the paired artificial muscle assembly 2000 within robotic arm 3000. The control system requires three control signals. AN, BN, and Vgoal, which are connected to terminals 90,91, and 92, respectively. AN and BN are control signals, shorthand for A-enable and B-enable, which determine which of the two opposed muscles are enabled at any given time; and Vgoal is an analog voltage between −Vcc and Vcc which represents a desired position of arm 3000.

Referring now to FIG. 9a, wiper voltage Vpot at the wiper terminal 94 of said potentiometer 22 is connected to both base terminals 76,77 of another instance of push-pull subcircuit 70. The collector of transistor 71 is connected to +Vcc, the collector of transistor 72 is connected to −Vcc, and reference terminal 79 is externally held at Vgoal.

An amplifier/buffer 96 has a large and predetermined voltage gain in the voltage range from −Vcc to Vcc and a current gain sufficient to drive solenoids 50,60a,b. Amplifier 96 is connected with load resistor 78 across its input terminals, with its negative terminal connected to terminal 79 and its positive terminal connected to terminal 73. Although amplifier/buffer 96 is not intended to be simply an operational amplifier (op-amp), those of average skill in the art will realize that an amplifier with the above described characteristics can easily be implemented using a common low-cost op-amp with suitable feedback.

The output terminal 98 of amplifier 96 is connected to the positive terminals 56,66,66 of valves 50,60a,60b, respectively. A diode 99 links negative terminal 57 of valve 50 to ground, with its anode connected to the negative terminal of valve 50, and its cathode connected to ground. The negative control terminals 67 of valves 60a,60b are connected to user-controlled signals AN and BN at input terminals 90 and 91, respectively.

Compressed air coming from a compressed air source through a hose 48 enters valve 50 through its pressure port 51. Port 52 of valve 50 is connected through hose 58 to input port 61 of valve 60a; port 53 of valve 50 is connected through hose 59 to input port 61 of valve 60b. Output port 62 of valve 60a is connected through hose 160 to bladder 120 of opposed muscle assembly 2000 within robotic arm 3000; output port 62 of valve 60b is connected through hose 260 to bladder 220 of opposed muscle assembly 2000 within robotic arm 3000.

FIG. 9b is a schematic diagram of a second, slightly-modified embodiment 100b of the novel control system of the present invention, also intended for use in controlling opposed artificial muscle assembly 2000 within robotic arm 3000. Control system 100b is identical in all respects to control system 100a shown in FIG. 9a, with the exception of the connections to the negative terminals 57 of valves 60a,60b. In control system 100b, rather than connect control signals AN and BN directly to the valve terminals, these signals are instead used to control two instances, 80a and 80b, of valve-control circuit 80 from FIG. 7. As described in the discussions of FIG. 7, each terminal 88 of subcircuits 80a,b is then connected to the negative terminal of the appropriate valve.

To be specific, control signal AN from terminal 90 is connected to input terminal 85 of valve control circuit 80a, and terminal 88 of circuit 80a is connected to negative terminal 67 of valve 60a. Similarly, control signal BN from terminal 91 is connected to input terminal 85 of valve control circuit 80b, and terminal 88 of circuit 80b is connected to negative terminal 67 of valve 60b.

FIG. 9c is a schematic diagram of a third, greatly simplified embodiment 100c of the novel control system of the present invention, intended for use in controlling opposed artificial muscle assembly 2000 within robotic arm 3000 when incompressible fluids are used in the artificial muscles. As discussed previously, in such a case a control system can be based on a single valve 50a including its third locking state. Although such a "hydraulic arm" is less able to accurately mimic biological motion, it is capable of accurate positioning and may be preferable for applications which do not require true biological motion, or when it is easier to provide a pressurized liquid than a compressed gas. Thus, simplified "hydraulic" control system 100c is included for completeness.

Control system 100c is identical in all respects to control system 100a shown in FIG. 9a, with the exception that valve 50a replaces valves 50,60a,60b, control signals AN and BN are no longer used, and new connections for the second solenoid terminals 56b,57b are added. Using incompressible fluids eliminates the need for signals AN and BN by removing several possible modes of operation of arm 3000; it is not necessary or desirable to be able to separately isolate one of the two bladders when the fluids are incompressible, so control signals AN and BN are not required.

Referring now to FIG. 9c, we see that the electrical circuit of control system 100c up through amplifier 96 is identical with and functions the same as that of system 100a of FIG. 9a. However, in control system 100c the output terminal 98 of amplifier 96 is connected to the positive terminals 56a and 56b of valve 50a. A diode 99a links negative terminal 57a of valve 50a to ground, with its anode connected to negative terminal 57a, and its cathode connected to ground. A second diode 99b links negative terminal 57b of valve 50a to ground, with its cathode connected to the negative terminal 57b, and its anode connected to ground. Pressurized incompressible fluid coming from a source of pressurized fluid through a hose 48a enters valve 50a through its pressure port 51a. Port 52a of valve 50a is connected through hose 160 to bladder 120 of opposed muscle assembly 2000 within robotic arm 3000; port 53a of valve 50a is connected through hose 260 to bladder 220 of opposed muscle assembly 2000 within robotic arm 3000. It is assumed that exhaust ports 54a,55a are connected, perhaps through hoses, to an unpressurized fluid reservoir from which a recirculating hydraulic fluid pump may draw fluid; this is the typical way that prior art hydraulic systems are arranged. This hydraulic fluid reservoir is analogous to the atmosphere for a compressed air system, where a compressor draws air in from the atmosphere and compresses it.

Operation—FIGS. 8,9abc—Improved Control Systems for Opposing Artificial Muscles

As described above in the discussions of FIG. 8, potentiometer 22 is located within pivot assembly 20 so that it turns when arm 3000 bends or extends. The end terminals of potentiometer 22 are connected to the positive and negative power supplies +/−Vcc with a polarity such that the voltage Vpot at wiper terminal 94 of potentiometer 22 decreases as arm 3000 extends, and increases as arm 3000 bends. Three variations of the novel control system are presented, as shown in FIGS. 9a,b,c.

The first variation, pneumatic control system 100a shown in FIG. 9a, is best suited for a system where considerable computing resources will be available for controlling the artificial muscle systems. This configuration allows the artificial muscles to be well controlled, but requires a considerable amount of rapid logic and decision-making at a higher level, presumably by a computer; muscle control signals AN and BN must be updated constantly to accurately mimic some of the biological modes.

The second variation, pneumatic control system 100b shown in FIG. 9b, is best suited for systems where minimal computer resources will be available for controlling the artificial muscles. None of the control signals need be updated very frequently, since the circuitry makes fine adjustments according to control signals AN and BN which now dictate only which "mode" the arm should use in its actions. The user or high-level controller or computer simply supplies an analog control signal Vgoal indicating a desired position, and two additional tri-state digital control signals AN and BN which tell the arm how the muscles should be used in reaching for this desired position. No further changes are then required in these control signals until the user desires a new position or wishes to switch to a new "mode".

The third variation, hydraulic control system 100c shown in FIG. 9c, is best suited for systems wherein the artificial muscles are driven by incompressible fluids—a "hydraulic arm" Control signals AN and BN are no longer required at all, since the various modes allowed by these signals don't make sense when using incompressible fluids.

The basic idea of all three versions of the new control system is to use a potentiometer physically mounted near pivot 20 as a way of measuring the position of robotic arm 3000, so that this low-cost, commonly-available component can be used as the basis for the feedback loop required for lifelike motion of the arm. The potentiometer is physically connected so that it turns and its wiper voltage decreases as arm 3000 extends; thus the wiper voltage Vpot represents the actual position of the arm within its range of motion. A voltage Vgoal representing a desired arm position is supplied by the user as the "goal" voltage that the wiper voltage should match when the arm is in the correct position. Using the wiper voltage as the input voltage to a class B output stage, but connecting the reference terminal to Vgoal rather than ground, a buffered "delta" control signal, which approximates the difference between the wiper voltage Vpot and Vgoal, is developed across the load resistor. However, because of the flat spot in the transfer characteristic of the class B output stage, this delta control signal remains near zero unless the wiper voltage differs by a "significant amount" from Vgoal. This results in a controlled sensitivity effect whereby the delta control signal does not increase noticeably unless a "significant" deviation in position is sensed. The delta control signal is connected to the input of an amplifier with a high voltage gain, adjusted so that when this control signal does rise to a "significant" level, the amplifier output voltage immediately swings to the appropriate rail (either +Vcc or −Vcc). This directional output is then used to selectively energize the appropriate valves (if they are enabled by the user) to correct the arm position back toward Vgoal.

With this improved control system, the robotic arm acts naturally. When Vgoal is changed, the arm moves toward the new desired position if sufficient force is available. The valves controlling the motion close just before the arm reaches that position, when the deviation between the actual and desired positions drops below a "significant" value. If the arm coasts a bit further, the control system does not bother correcting it unless this new deviation in the opposite direction becomes "significant".

If a new force is applied to the arm after it is positioned, the control system ignores changes in position which are less than a small "significant" change determined by the flat spot in the transfer curve. It then acknowledges or "senses" that there has been a deviation and responds with signals which, if enabled, will open the correct valves needed to resist the new deviation and force the arm back in position. In the pneumatic control systems 100*a,b*, either artificial muscle may be disabled so that the motion is entirely due to the action of the remaining muscle.

Referring now to FIG. 9*a,* we see that the end terminals of potentiometer 22 are connected to the positive and negative power supplies +/−Vcc. The polarity of connection and mounting direction chosen are such that the voltage Vpot at wiper terminal 94 of potentiometer 22 decreases as arm 3000 extends, and increases as arm 3000 bends. Advantageously, potentiometer 22 should be chosen so that the range of motion of arm 3000 corresponds to the full voltage swing from −Vcc to +Vcc.

The configuration of subcircuit 70 in FIG. 9*a* is equivalent to the circuit of FIG. 5*b*. However, in this case wiper voltage Vpot at wiper terminal 94 takes the place of Vi in FIG. 5*b,* and reference terminal 79 is connected to Vgoal. We can safely ignore current flowing into high-gain amplifier 96. So from the discussion of FIGS. 5*b,c,* we expect a transfer characteristic similar to FIG. 5*c,* centered around Vgoal. In other words, the voltage across the input of amplifier 96 is nearly zero until Vpot deviates from Vgoal by a "significant" amount in either direction, at which point it rises sharply in proportion to further deviations between the two voltages.

High-gain amplifier/buffer 96 has a predetermined voltage gain in the voltage range from −Vcc to Vcc. Amplifier/ buffer 96 has several rather strict requirements: 1) it needs to have a large voltage gain so that its output swings to the rails for any "significant" deviation; 2) it needs to have a fairly-large output current drive capability so that it can drive the solenoid valves directly, 3) it should have a good common-mode rejection ratio so that it will react the same to the same deviation of Vpot from Vgoal even when Vgoal approaches +Vcc or −Vcc, and 4) it should be relatively insensitive to noise, so that it will not switch the valves back and forth needlessly in a noisy environment. Although these requirements sound difficult to attain, one of average skill in the art will realize that they are all in fact attributes of well-known circuits based on commonly-available op-amps. The voltage gain is selected so that when the deviation in small, output terminal 98 remains near ground, but when the voltage at the input of the amplifier begins to rise sharply due to a significant deviation, it is immediately amplified so that output terminal 98 swings to the appropriate rail. From FIG. 9*a,* we see that output terminal 98 will swing to +Vcc when Vpot is significantly greater than Vgoal, and that output terminal 98 will swing to −Vcc when Vpot is significantly less than Vgoal.

Output terminal 98 is connected to the positive terminals of each solenoid valve in FIG. 9*a.* Because of diode 99, valve 50 can only be energized when terminal 98 swings to +Vcc, otherwise, valve 50 stays in its "resting" state.

Now assume for the moment that control signals AN and BN are both grounded; in this state, both valves 60*a,*60*b* are enabled. If Vpot and Vgoal do not differ significantly, then terminal 98 remains near ground, and valves 60*a,*60*b* are both isolated so that no air can flow, the arm will remain where it is. If Vpot is significantly greater than Vgoal, then we can see that arm 3000 has bent too far. Terminal 98 rises to +Vcc, which connects both valves 60*a,*60*b* and switches valve 50 to the energized state, which exhausts bladder 120 by connecting hose 160 to exhaust port 54 (EA), and pressurizes bladder 220 by connecting hose 260 to pressure port 51. This moves arm 3000 back from its "over-bent" position until the deviation again becomes "insignificant" when the input to amp 96 falls near zero and output terminal 98 falls back to ground. Now consider what will happen if Vpot is significantly less than Vgoal. Then we can see that arm 3000 has extended too far. Terminal 98 falls to −Vcc, which connects both valves 60*a,*60*b* but leaves valve 50 in its de-energized state. This exhausts bladder 220 by connecting hose 260 to exhaust port 55 (EB), and pressurizes bladder 120 by connecting hose 160 to pressure port 51. This moves arm 3000 back from its "over-extended" position until the deviation again becomes "insignificant" when the input to amp 96 rises to near zero and output terminal 98 rises back to ground.

Already, with both secondary control signals AN and BN constantly enabled, circuit 100*a* provides a control system which is far superior to the coarse-control or arm-in-motion systems discussed previously. Using circuit 100*a* to control the previously-described 5-port, 3-position solenoid valve 50*a* will yield a control system equivalent to this single state of the improved control system (this is shown in FIG. 9*c* and will be discussed further below). Yet for the new control system, there are further control possibilities if one or both of AN, BN are floated rather than grounded, particularly if this can be changed frequently under computer control.

With AN floating, valve 60*a* isolates bladder 120 from valve 50 so that no air can enter or leave bladder 120, regardless of the state of valve 50. Similarly, floating BN makes valve 60*b* isolate bladder 220 from valve 50 so that no air can enter or leave bladder 220. This additional control can be used to further mimic biological control modes if a computer-controlled system is employed. For example, if the computer continually estimates the air which is present in each bladder, and keeps track of the motions of the arm, then valves 60*a* and 60*b* can be used as a computer-controlled means to determine when the amount of air in each bladder is allowed to change. Of course, this method does involve considerable characterization of the artificial muscles, valves and flow rates, and may use significant computer resources. And using this method, the computer must change one of control signals AN and BN each time one of valves 60*a,b* is enabled or disabled. With this system, AN and BN are constantly changing under computer control.

Alternate circuit 100*b* shown in FIG. 9*b* allows a user to mimic biological motions without requiring significant computer resources for control or detailed characterization of the arm and its components. Circuit 100*b* is identical to circuit 100*a* except that rather than connecting control signals AN, BN directly to valves 60*a,b*, these control signals are instead used to control two valve-control subcircuits 80*a,b* which in turn control valves 60*a,b*, respectively. The two valve-control subcircuits 80*a,b* allow the muscles to be controlled in much the same manner as biological muscles are controlled. Valves 60*a,b* are automatically enabled and disabled by subcircuits 80*a,b*, perhaps many times, in accordance with the control signals AN and BN which now are high-level command signals which need be changed only occasionally.

Recall from the discussions of FIG. 7 that circuit 80 enables a solenoid valve for voltages at the positive terminal of the solenoid valve of. 1) only +Vcc if terminal 85 is held high (above ground); 2) only −Vcc if terminal 85 is held low (below ground); and 3) either +Vcc or −Vcc if terminal 85 is grounded or floating.

Referring now to FIG. 9*b*, we see that valve-control subcircuit 80*a* controls valve 60*a*, and valve-control subcircuit 80*b* controls valve 60*b*. Each of circuits 80*a* and 80*b* has 3 states, so there are as many as 9 separate control modes with this control system. The functions of each are enumerated below.

A) First consider the case where control signals AN and BN are both grounded (or floating), so that valves 60*a,b* are always enabled. This is the same as the circuit of 9*a* when both valves are enabled; it is already a better control system than the coarse controls discussed previously. This mode is a useful general-purpose positioning mode, equivalent to biological mode 3).

B) AN grounded; BN high. Now the "artificial biceps" is fully enabled for either inflation or deflation of bladder 120 through valve 60*a*, but the "artificial triceps" is enabled only for conditions which would further inflate bladder 220, increasingly tensing the triceps against the biceps.

C) AN grounded; BN low. Now the "artificial biceps" is fully enabled for either inflation or deflation of bladder 120 through valve 60*a*, but the "artificial triceps" is enabled only for conditions which would deflate bladder 220, keeping the triceps as relaxed as possible. This useful mode corresponds to curling a barbell, and is equivalent to biological arm mode 1)

D) AN high; BN grounded. Now the "artificial triceps" is fully enabled for either inflation or deflation of bladder 220 through valve 60*b*, but the "artificial biceps" is enabled only for conditions which would further inflate bladder 120, increasingly tensing the biceps against the triceps.

E) AN high; BN high. Now both the "artificial triceps" and the "artificial biceps" are enabled only for conditions which would further inflate bladders 120 and 220, increasingly tensing the biceps against the triceps. As the arm homes in on its desired position, the pressure keeps increasing in both bladders. Eventually, the arm will be located at or near the desired position, with both bladders inflated to the pressure of the pressure source. This useful mode represents the isometric "locked arm" configuration, biological mode 4).

F) AN high; BN low. Now the "artificial biceps" is enabled only for conditions which would further inflate bladder 120, but the "artificial triceps" is enabled only for conditions which would deflate bladder 220, keeping the triceps as relaxed as possible. This mode corresponds to curling a barbell but allows for no correction if bladder 120 becomes overinflated inadvertently; mode C) will be superior in most cases.

G) AN low, BN grounded. Now the "artificial triceps" is fully enabled for either inflation or deflation of bladder 220 through valve 60*b*, but the "artificial biceps" is enabled only for conditions which would deflate bladder 120, keeping the biceps as relaxed as possible. This useful mode corresponds to reverse curling a barbell, and is equivalent to biological mode 2).

H) AN low; BN high. Now the "artificial triceps" is enabled only for conditions which would further inflate bladder 220, but the "artificial biceps" is enabled only for conditions which would deflate bladder 120, keeping the biceps as relaxed as possible. This mode corresponds to reverse curling a barbell but allows for no correction for an overinflated bladder 220; mode G) will be superior in most cases.

I) AN low; BN low. Both the artificial biceps and triceps are enabled only for conditions which will deflate both bladders. Without relying on previous inflation of the bladders, there is no reason to assume that the arm will be controllable in this state. This mode is useful only if the user desires to fully relax the arm, equivalent to biological mode 5).

One of ordinary skill in the art will see that an arm controlled by circuit 100*b* will require much less supervision by the user or a high-level controller than an arm controlled by circuit 100*a*. Although circuit 100*a* can also reproduce all of the 9 modes just listed above (and perhaps other more unusual modes), most of these modes will require considerable monitoring of the arm and frequent enabling and disabling of valves 60*a,b* (each time requiring a high level command) to match how they are automatically controlled by subcircuits 80*a,b* of circuit 100*b*. Control systems based on circuit 100*a* basically allow the arm to be controlled in software rather than hardware, but unless there is tremendous computing resources available, such software-based control systems may react slower than the hardware solution provided by circuit 100*b*. Circuit 100*b* already mimics the five most common biological modes, as well as providing four less commonly used modes. So control circuit 100*b* is probably the preferred solution unless the user foresees that: 1) frequent changes to the control modes will be needed (which are easier to modify in software); 2) the application does not require particularly fast response from the control system; or 3) the application requires other control modes than are provided by circuit 100b.

Now referring to FIG. 9c, the operation of simplified control system 100c for use with incompressible fluids may be discussed. Output terminal 98 is connected to both positive terminals 56a,56b of solenoid valve 50a in FIG. 9c. Because of diode 99a, the first solenoid of valve 50a can only be energized when terminal 98 goes to +Vcc. Because of diode 99b, the second solenoid of valve 50a can only be energized when terminal 98 goes to −Vcc. Otherwise, valve 50a stays in its isolated state.

If Vpot and Vgoal do not differ significantly, then terminal 98 remains near ground, and valve 50a is isolated so that no fluid can flow, the arm will remain (solidly locked) where it is. If Vpot is significantly greater than Vgoal, then we can see that arm 3000 has bent too far. Terminal 98 rises to +Vcc, which energizes the first solenoid of valve 50a; this exhausts bladder 120 by connecting hose 160 to exhaust port 54a (EA), and pressurizes bladder 220 by connecting hose 260 to pressure port 51a. This moves arm 3000 back from its "over-bent" position until the deviation again becomes "insignificant" when the input to amp 96 falls near zero and output terminal 98 falls back to ground. Now consider what will happen if Vpot is significantly less than Vgoal. Then we can see that arm 3000 has extended too far. Terminal 98 falls to −Vcc, which energizes the second solenoid of valve 50a. This exhausts bladder 220 by connecting hose 260 to exhaust port 55a (EB), and pressurizes bladder 120 by connecting hose 160 to pressure port 51a This moves arm 3000 back from its "over-extended" position until the deviation again becomes "insignificant" when the input to amp 96 rises to near zero and output terminal 98 rises back to ground.

One final detail remains in describing the operation of circuits 100a,b,c; a careful reader will have noticed that the term "significant deviation between Vpot and Vgoal" has been carefully left undefined up to this point. This is important because it determines how accurately arm 3000 may be positioned using the novel control system of the present invention. And in general, it is not desirable to have a smaller positioning accuracy than is actually required for a particular application; in many cases this will just lead to more oscillations if the arm overshoots slightly in searching for an "acceptable" match between Vpot and Vgoal. A positioning accuracy just barely fine enough to meet the needs of the application will result in the fewest possible positioning corrections, the fewest actuations of the valves, and the lowest use of power and compressed air.

A first order analysis of subcircuit 70 within control systems 100a,b,c, like that analysis given in the discussions of FIGS. 5abc and 6ab, would indicate that a significant deviation would be approximately 0.7V. This is the textbook approximation usually given for predicting the turn-on voltage of a silicon diode or the base-emitter voltage at which a silicon bipolar transistor enters its forward-active region of operation. To estimate the positioning accuracy achievable if this approximation holds, one can plug in a few real-world numbers. For example, DC solenoid valves operating at 12V or 24V are commonly available. Optimally, one would use power supplies of +/−Vcc=+/−24V and select potentiometer 22 so that wiper voltage Vpot could swing from +24V to −24V in traveling across its range of motion. Assuming that arm 3000 can be extended to the straight position and bent to a 90 degree angle, then the voltage sensitivity of Vpot to angular motion is about 0.53V/deg. Thus, if the above first-order approximation of a significant deviation being 0.7V holds, then given these assumptions, this corresponds to a positioning accuracy of about 1.3 degrees of arc. If this is a finer tolerance than is desired, then the optional circuits described in the discussions of FIG. 6ab can be used to increase the size of an ignored deviation.

However, if an even finer positioning tolerance is required, then one must look closer at the assumptions behind the first-order analysis. Diodes and bipolar transistors do not actually have a sharp turn-on in current at 0.7V as the first-order theory states. In actuality, the currents through both are exponential functions of the appropriate bias voltage. The 0.7V turn-on approximation, if strictly stated would be: "silicon diodes or bipolar transistors of typical sizes fabricated using standard processes will start to conduct currents which in most circuits would be considered significant at about 0.7V". This is quite different from a sharp turn-on at 0.7V. In fact, in circuits 100a,b the positioning accuracy is a design target which can be achieved through several design techniques.

First, it is important to determine what current is actually needed to swing the output of amplifier 96 to the rail. If amplifier 96 has a voltage gain of Aamp, and we add a guardband of a factor of 2, then the minimum current Isw required to pass through a minimally turned-on transistor (either 71 or 72) in order to barely switch the amplifier output to a rail must be approximately Isw>2Vcc/ (R*Aamp). So the required current can be reduced by either increasing the value of R (resistor 78) or the voltage gain of amplifier 96. And since this current is the result of an exponential function of the deviation voltage, large changes in R or Aamp can be made while still keeping the positioning accuracy small and very predictable. Finally, this exponential function also has a multiplier which is determined by the physical characteristics of the bipolar transistors, so even the particular transistor used can be changed in order to help determine the turn-on voltage of the base-emitter junctions.

In fact, one of ordinary skill in the art will see that the positioning accuracy can even be made adjustable if desired, by replacing resistor 78 with another potentiometer, or providing an amplifier 96 with a programmable gain. This refinement might well be worthwhile; if fine positioning is only required occasionally, the positioning accuracy can be left at a relatively-coarse level for day-to-day use, and then refined down to pinpoint positioning accuracy when required.

Conclusion, Ramifications, and Scope

Accordingly, the reader will see that the artificial muscle, opposed pair of artificial muscles, robotic arm and novel control systems of the present invention act in concert to provide all of the elements needed to build robust, low-cost exoskeletal robots and robotic limbs The artificial muscles of the present invention form lightweight, compact linear actuators which mimic the actions of organic muscles and have comparable or greater strength and speed than organic muscles of similar size. The artificial muscle requires an exoskeletal pipe to contain the muscle and form a rigid base upon which the muscle acts. However, in general this pipe is not considered a part of the artificial muscle but instead takes the place of the endoskeletal bone which an analogous biological muscle would act against. Typically, the pipe will be chosen from among the coexisting structural members in the design application.

The artificial muscles of the present invention provide motion by pulling on cables or "artificial tendons" through ranges of motion similar to those of organic muscles; and also like organic muscles, the available force is greatest when the muscle is at full extension, falling as the muscle contracts. The artificial muscles of the present invention are particularly simple and may be easily manufactured for low cost Unlike competing technologies which result in overcomplicated and heavy solutions, the artificial muscles of the present invention do not rely on electromagnetic effects for their motive force and so contain no electric motors. The new artificial muscles with their novel pneumatic approach are capable of holding at a variety of positions without drawing significant power.

And the artificial muscles of the present invention require no exotic or unusual properties of the materials used in their construction. Since low-cost materials with the required properties have been long known to provide long-term reliability in applications requiring similar properties, the muscle analogs of the present invention should provide reliability comparable with all competing prior-art technologies, and far exceeding the reliability of the prior-art McKibben muscle technology. Although the McKibben muscle is the most similar prior-art technology to the present invention and enjoys many of the same advantages in terms of inherent design superiority, the McKibben muscle's requirement for exotic material properties has limited its reliability and prevented its widespread adoption ever since its invention. But because of the present invention's reliance instead on readily available low cost materials of proven reliability, the artificial muscle of the present invention overcomes this limitation and provides a similar yet superior solution with inherently better reliability than the McKibben muscle.

When mounted in opposing pairs within an exoskeletal bone with an appropriately-shaped interior surface (such that two bladders can be mounted opposing each other, each when inflated forcing their cable to deviate from its shortest path), such as straight pipes, the artificial muscles of the present invention provide a simple, low-cost method of providing motive force to robust, reliable exoskeletal robotic limbs. Mounted inside the same pipe in physical opposition, the muscles even interact synergistically and assist each other when one bladder inflates as the opposing bladder is being vented. When used in applications such as robotic limbs which usually include hollow pipe-like structural elements anyway, the artificial muscles can be built into these already-existing pipes so that no additional pipe is needed to support or encase the muscles. Each opposing pair of artificial muscles is sufficient to control the motion of one pivot or joint along with its lever capable of rotating around this joint in either direction.

A simple, low-cost method of controlling such opposed pairs of pneumatic artificial muscles is also provided in two main forms: a first form is well suited for systems with much high-level supervision, probably by a computer; and a second form is provided for cases where only limited high-level supervision of the arm will be available. A third simplified form is also provided, suitable only for systems using essentially incompressible fluids.

Taken together, the artificial muscle, opposed pair of artificial muscles, robotic arm and novel control systems of the present invention provide all of the elements needed to build robust, low-cost exoskeletal robots. One can envision sets of multi-jointed exoskeletal leg assemblies formed of jointed pipe, providing mobility to robots that mimic insects or spiders; and accurately-controllable arms can be built and mounted on such robots to provide a capability to manipulate their environment. Or easily-controlled, low-cost stationary arms or manipulators can also be built, with capabilities similar to those of heavy and complicated prior-art arms based on electric motors.

Although shown in their simplest linear form, the artificial muscles of the present invention may be fabricated in a variety of ways, depending on the requirements of the design. For example, increasing just the distance between the bladder and the cable positioning means will increase the available tension on the cable at the expense of decreasing the distance the cable is pulled in. Or, if single artificial muscles are desired, they might be built inside hollow members with essentially-arbitrary interior surfaces (as long as inflating the bladder between said surface and said cable forces the cable to deviate from its shortest path). Such shapes as curved or even helical pipes (with the cable positioning means placed along the inside of the curvature) may be used in order to create compact muscles that yet are able pull the cable a large distance. Pipes can even be built with cable positioning means spaced along their length, alternating with bladders inserted between them, so that if a single cable ran in a straight line over all the deflated bladders, it would be pulled in a very large distance if they were all inflated. And if the different bladders were individually controlled, the distance that the cable was pulled would depend on how many bladders were activated, creating a new and different control method. Clearly, many variations on the enclosed exoskeletal artificial muscle theme of the present invention are possible And although the primary focus of the previous discussions has been pneumatically-driven artificial muscle assemblies, the present invention applies equally well if other fluids, perhaps even substantially incompressible fluids such as water or hydraulic fluid, are used to fill the bladders. Although such "hydraulic" muscles have their limitations and will be less able to closely mimic biological motion, there are applications where incompressible fluids might be preferable. For example, powerful and heavy duty remote-controlled firefighting robots might be built, capable of dragging a firehose behind them and using the high-pressure water from the firehose for their motive force as well as to fight the fire. Naturally, different valves would necessarily be used for the higher-viscosity fluids in order to achieve the required level of flow. And of course, simplified hydraulic control system 100c would be sufficient to control the paired artificial muscles in this case. But such a remote-controlled robot, perhaps built of insulated steel, cooled and powered by water from the firehose, and requiring no oxygen, would surely be capable of entering and withstanding hellish conditions no fireman could survive. Such a remote-controlled robot could fight fires from within and even help rescue fire victims in extreme conditions, the robot could scout the fire interior, bring safety equipment and breathing apparatus to trapped victims, and let firefighters know if there were survivors to rescue before they risked their lives entering extremely hazardous fires. In such an application, the present invention could help save the lives of both fire victims and firefighters.

Alternatively, padded and shaped pipe-like members resembling human limbs might be used to enclose muscle assemblies of the present invention within low-cost prosthetic applications. The opposed pairs of artificial muscles of the present invention with their associated novel control system closely mimic natural biological motions, making them ideal for this application. And of course, since extremely high forces are not a requirement for this prosthetic use, the exoskeletal pipe-like members need not be made of steel or other massive metals, light composite materials can be used, providing lightweight and comfortable prosthetics for accident survivors. Lightweight powered prosthetic limbs become a real possibility using the present invention. With an appropriate high-level control system directing all of the required opposing muscle pairs in concert, one can envision the present invention being used to help paraplegics or even quadriplegics to walk again, prosthetically. Even a powered prosthetic arm and hand could be built using the present invention, replacing each biological opposed muscle pair with an appropriately-sized opposed artificial muscle pair.

Yet even these robotic and prosthetic applications do not bound the possible uses of the present invention. Because of the extreme simplicity and accompanying low cost of this artificial muscle, applications where powered motion might not normally be considered become practical. For example, using small-diameter pipes and a tiny electronic controller of limited intelligence, one could build self-erecting tents. And since the available force scales up roughly in proportion to the length of the bladder, and again in proportion to the inner diameter of the pipe, the force necessary to "scale up" such dwellings to a much larger size would also be available. In real-world terms, one can envision large, temporary tent-like structures, radially-symmetric and perhaps hemispherical in shape; the frame might be formed using ribs or "legs" built of jointed sections of large-diameter steel or aluminum pipe (for example, 3 or 4 inches in diameter) connected to a centralized "hip assembly" at the apex. Using the present invention, such a structure could be built with artificial muscles enclosed within the ribs, so that the ribs would be individually and collectively moveable; the large, strong artificial muscles in this case might be built using closed sections of firehose for bladders and steel cables for tendons. Again with the appropriate high-level controller (and a big air compressor), one can envision driving up to a job site with the frame folded compactly on a flatbed truck, and having the frame "climb down" from the truck bed, walk over to the desired erection site, and set itself up. Such a structure would not require a crane or other machine to lift the ribs, or human workers to perform the dangerous aerial work of assembling the frame. Most of the heavy work in setting up such a temporary structure would be performed by the artificial muscles.

And of course, once the technology is in place for erecting such temporary dome structures quickly, safely and easily, the idea of adapting such technology for permanent construction comes to mind. Geodesic domes are another idea that has not achieved widespread use despite inherent superiorities in design, particularly in efficient use of materials and low power consumption. This is probably due to the difficulty and unfamiliarity of construction using non-Manhattan geometries (not right angles), and to the numerous odd-angled joints in a hemispherical roof constructed from flat polygonal panels. But if a factory-built prefabricated frame were available, complete with pre-installed and pre-measured mounting fixtures designed to enable easy on-site final assembly, and if such a frame was capable of erecting itself, the only limiting factor would be whether the technology included could pay for itself in a single use. Such a frame might be practical even if used merely as scaffolding surrounding a structure being built using standard construction techniques, perhaps with one or more of the legs configured to act as a crane during assembly. Surely the present invention could find widespread applications in a number of industries, even in the construction industry.

Even self-erecting temporary bridges might be built using the present invention, looking and walking like a centipede or caterpillar. Such a bridge might be quite useful in rough terrain or during floods or seasonal storms. One can imagine a convoy driving up to a river with such a bridge on the lead truck, and having the bridge climb down and erect itself, after the convoy passes, the bridge could climb back up onto the truck as the convoy continues.

Finally, although one of the most basic concepts of the present invention is the superiority of an exoskeletal arrangement of the artificial muscles, it is by no means a physical limitation of the technology. If for some reason, despite the disadvantages, an engineer was determined to build a design using members with open cross sections such as I-beams, one of average skill in the art can easily see how the artificial muscle of the present invention could be mounted, perhaps in the I-beam channel, to achieve the same effect as shown in the above specification. The only difference would be that the bladder would definitely have to be able to withstand the working pressure along its entire surface rather than just at the ends (and of course that the muscle would be exposed to the potentially hazardous environment).

Thus, the scope of the invention should be determined by the appended claims and their legal equivalents, rather than by the examples given.

I claim:

1. An artificial muscle analog for mimicking an organic muscle, substantially disposed within a void or cavity, defined by an interior surface, within a first substantially rigid member or exoskeletal bone, comprising;
    a substantially flexible artificial tendon or cable of diameter substantially less than the dimensions of said cavity, having a first fixed end and a second free end, disposed substantially within said cavity;
    a plurality of cable constraint points for constraining the motion of said cable, each located on said interior surface, including at least a pair of constraint points comprising a first fixed cable constraint point and a second sliding cable constraint point;
        wherein said fixed end of said cable is affixed to said bone at said fixed constraint point;
    a low-friction roller, guide or cable positioning means disposed near said sliding cable constraint point, whereby said cable is constrained to pass near said point, said means nevertheless allowing said cable to slide freely past said point with relatively little friction;
        whereby a shortest cable path is defined, it being the unobstructed path followed by said cable from said first point to said second point within said cavity when said cable is taut;
    an inflatable bladder, affixed to said interior surface and placed such that said bladder forces said cable to deviate from said shortest cable path, when inflated; and
    a valve or connection means whereby said bladder may be connected to a pressurized fluid;
        wherein the pressure of said fluid may be greater than the pressure of said bladder;
        whereby fluid is forced into said bladder when said valve is connected, thereby inflating the bladder;
        whereby said inflating bladder forces said cable to deviate from said shortest path;
        whereby the length of cable between said first and second constraint points is forced to increase;
        whereby, said cable being fixedly constrained at its first end to said first constraint point, and slidingly constrained at said second constraint point, said free end of said cable is pulled in under tension;

whereby said artificial muscle acts like said organic muscle when tensed; and wherein the pressure of said fluid may be less than the pressure of said bladder;

whereby fluid is forced out of said bladder when said valve is connected, thereby deflating said bladder;

whereby said deflating bladder allows said cable to approach said shortest path;

whereby the length of cable between said first and second constraint points is allowed to decrease;

whereby, said cable being fixedly constrained at its first end to said first constraint point, and slidingly constrained at said second constraint point, said free end of said cable may be pulled out, under reducing tension;

whereby said artificial muscle acts like said organic muscle when relaxed;

whereby said artificial muscle analog mimics said organic muscle.

2. The artificial muscle analog of claim 1:

wherein said bladder is substantially flexible, but not significantly stretchable.

3. The artificial muscle analog of claim 1:

wherein said bone comprises a hollow cylindrical pipe;

wherein said interior surface comprises the cylindrical interior surface of said pipe;

wherein said bladder is shaped substantially like a tubular length of hose with a constant outer diameter and closed ends;

wherein the outer diameter of said hose is not less than the interior diameter of said pipe;

such that said pipe supports said bladder when inflated, excepting said closed ends.

4. The artificial muscle analog of claim 1, wherein said bladder completely fills said cavity when fully inflated;

whereby said cavity fully supports said inflated bladder.

5. The artificial muscle analog of claim 1, wherein said fluid is essentially incompressible.

6. The artificial muscle analog of claim 1 wherein said muscle analog forms a first or primary muscle analog within said cavity, further comprising a secondary or opposed muscle analog according to claim 1, also disposed within said cavity;

wherein said primary and opposed muscle analogs are placed in physical opposition to one another within said cavity;

such that if either bladder, when inflated, impinges on the cable of the other muscle analog, said bladder pushes said cable toward its said shortest cable path; and such that if one bladder, when inflated, impinges on the other bladder, said one bladder assists in forcing fluid from said other bladder if its said connection means are connected, thereby helping to deflate said other bladder;

whereby said primary and opposing artificial muscle analogs synergistically assist in each others operation when used to mimic opposing muscle groups.

7. The artificial muscle analog of claim 1:

wherein the first and second cable constraint points are placed such that the geodesic defined on said interior surface by said points substantially coincides with said shortest cable path;

such that said cable, if held taut between said first and second cable constraint points, unobstructed within said cavity, runs substantially along said interior surface, substantially tracing said geodesic;

wherein said bladder is affixed to said interior surface along said geodesic, between said interior surface and said cable.

8. The artificial muscle analog of claim 7 wherein said muscle analog forms a first or primary muscle analog within said cavity, further comprising a secondary or opposed muscle analog according to claim 7, disposed within the same cavity;

wherein said pair of cable constraint points of said primary and opposed muscle analogs are the primary and opposed pair of said points, respectively;

wherein said primary and opposed pairs of points define, on said interior surface, primary and opposed geodesics, respectively;

wherein each of said geodesics is substantially coincident with the shortest unobstructed cable path within said bone connecting its defining pair of points;

wherein said interior surface of said bone is shaped such that said primary and opposed geodesics may be located in physical opposition to one another;

such that when the primary bladder inflates, it pushes the bladder and cable of said opposed muscle analog toward said opposed geodesic; and such that when the opposed bladder inflates, it pushes the bladder and cable of said primary muscle analog toward said primary geodesic;

whereby said primary and opposed artificial muscle analogs synergistically assist in each others operation when used in opposition to mimic opposing muscle groups.

9. The primary and opposing muscle analogs of claim 8, disposed within said exoskeletal bone, which bone forms an upper arm, further comprising:

a substantially rigid forearm, second member or second bone, pivotally connected to said upper arm by a pivotal elbow joint having an axis, such that said forearm may rotate with respect to said upper arm around said axis of said elbow joint;

wherein the free end of said primary cable is affixed to said forearm at a first offset point, radially displaced from said axis, chosen to induce rotation of said forearm around said axis in one direction when said free end is pulled in under tension; and wherein the free end of said opposed cable is affixed to said forearm at a second offset point, radially displaced from said axis, chosen to induce rotation of said forearm around said axis in the opposite direction when said free end is pulled in under tension;

whereby an artificial arm is formed, in which said muscle analogs control the rotation of said forearm about said elbow, thereby mimicking an organic arm controlled by its opposed muscle groups.

10. The artificial arm of claim 9, further comprising a first fluid reservoir having a first pressure and a second fluid reservoir having a second pressure;

wherein the connection means of said primary muscle analog may be controlled using a primary variable control signal which can be varied;

such that when said control signal is greater than a first upper threshold value, said connection means connects said primary bladder to said first reservoir; and such that when said control signal is less than a first lower threshold value, said connection means connects said primary bladder to said second reservoir;

wherein the connection means of said opposed muscle analog may similarly be controlled using a opposed variable control signal which can be varied;

such that when said control signal is greater than a second upper threshold value, said connection means connects said opposed bladder to said second reservoir; and such that when said control signal is less than a second lower threshold value, said connection means connects said opposed bladder to said first reservoir.

11. The artificial arm, pressurized fluid reservoirs, control signals and threshold values of claim 10 wherein said first pressure is greater than the pressure within said cavity, and said second pressure is less than the pressure within said cavity;

whereby said primary bladder may be inflated by connecting it to said first reservoir, and deflated by connecting it to said second reservoir; and whereby said opposing bladder may be inflated by connecting it to said first reservoir, and deflated by connecting it to said second reservoir.

12. The artificial arm, pressurized fluid reservoirs, control signals and threshold values of claim 11 wherein said primary control signal and said opposed control signal each equals an overall common control signal, whereby said primary and opposed muscle analogs automatically act in concert with one another.

13. The artificial arm, pressurized fluid reservoirs, control signals and threshold values of claim 12:

wherein said first and second upper threshold values both equal a common upper threshold value; and wherein said first and second lower threshold values both equal a common lower threshold value;

whereby the bladders of said primary and opposed muscle analogs are simultaneously inflated and deflated, respectively, when said common control signal exceeds said common upper threshold value; and whereby the bladders of said primary and opposed muscle analogs are simultaneously deflated and inflated, respectively, when said common control signal falls below said common lower threshold value;

whereby said common control signal and reservoirs together form an automatically coordinated control means for controlling said connection means of said muscle analogs and thereby said muscle analogs.

14. The artificial arm, pressurized fluid reservoirs, control signals and threshold values of claim 13, further comprising:

a measurement means for measuring the rotational position of said forearm, which produces a measured positional signal which corresponds to the measured rotational position of said forearm according to a first predetermined relationship between said position and said signal;

a variable target positional signal which may be varied, representing a target rotational position of said forearm according to said first predetermined relationship;

whereby if said arm is in said target position, said measurement means produces said target signal;

a differential amplifying means with two inputs, for amplifying the difference between two input signals, whose two inputs are said measured positional signal and said target positional signal, and whose output is the amplified difference between them;

wherein said amplifying means has an upper compliance limit and a lower compliance limit which its output cannot exceed; and wherein said amplifying means also has an input sensitivity below which its output does not vary significantly from its value when said input signals are identical;

such that when said target signal and measured signal differ by less than said sensitivity, said output remains the same as if said signals were equal;

whereby said output, being amplified, rapidly approaches said upper compliance limit when said difference, of one polarity, exceeds said sensitivity, and rapidly approaches said lower compliance limit when said difference of the opposite polarity exceeds said sensitivity;

wherein said upper compliance limit exceeds said upper threshold value and said lower compliance limit exceeds said lower threshold value;

whereby if said output signal forms said common control signal, said target and measured signals may be connected to said inputs with polarity chosen such that both of said muscle analogs act in concert to reduce said difference to below said sensitivity;

whereby an automatic control system for said arm is formed such that said muscle analogs automatically attempt to keep the measured position of said arm at said target position, within said sensitivity.

15. The artificial arm, pressurized fluid reservoirs, control signals and threshold values of claim 13, wherein said fluid comprises is significantly compressible, further comprising:

a primary enabling control signal, wherein the connect means of said primary muscle analog connects the bladder of said primary muscle analog to one of said reservoirs only if said enabling control signal exceeds a primary enable threshold value; and an opposed enabling control signal, wherein the connect means of said opposed muscle analog connects the bladder of said opposed muscle analog to one of said reservoirs only if said enabling control signal exceeds an opposed enable threshold value;

whereby said automatically coordinated control means provides greater control of said muscle analogs.

16. An artificial muscle analog for mimicking an organic muscle, substantially disposed within a void or cavity, defined by an interior surface, within a first substantially rigid member or exoskeletal bone, comprising;

a substantially flexible artificial tendon or cable of diameter substantially less than the dimensions of said cavity, having a first fixed end and a second free end, disposed substantially within said cavity;

a plurality of cable constraint points for constraining the motion of said cable, each located on said interior surface, including a first fixed cable constraint point and a group of one or more second sliding cable constraint points;

wherein said fixed end of said cable is affixed to said bone at said fixed constraint point;

a group of one or more low-friction rollers, guides or cable positioning means, each disposed near a different one of said sliding cable constraint points, whereby said cable is constrained to pass near each said sliding point, each of said guides nevertheless allowing said cable to slide freely past the point near said guide with relatively little friction;

whereby a shortest cable path is defined, it being the unobstructed path followed by said cable when taut, from said first point through each of said guides, thereby passing near each of said second points within said cavity;

a group of one or more inflatable bladders, each affixed to said interior surface, each said bladder placed such that it forces said cable to deviate from said shortest cable path, when inflated; and a plurality of valves or connection means whereby one or more of said bladders may be selectively connected to ones of pressurized fluid reservoirs selected from a group of one or more pressurized fluid reservoirs.

17. A control means for controlling a first or primary pneumatic or hydraulic actuator and a second or opposed pneumatic or hydraulic actuator, said actuators being of arbitrary type, which actuators are arranged so as to act in opposition to one another to control the motion of an object, said actuators having a first port and a second port whereby pressurized fluids may be connected to said first and second opposing actuators, respectively, comprising:

a first fluid reservoir having a first high pressure and a second fluid reservoir having a second low pressure, said high pressure being greater than said low pressure;

a first or primary connection means whereby either reservoir may be selectively connected to said first port, which is controlled using a primary variable control signal which can be varied;

such that when said control signal is greater than a first upper threshold value, said connection means connects said first port to said first reservoir;

whereby said high pressure fluid attempts, through said first actuator, to move said object in a first direction; and such that when said control signal is less than a first lower threshold value, said connection means connects said first port to said second reservoir;

whereby said low pressure fluid attempts, through said first actuator, to move said object in the opposite direction;

a second or opposed connection means whereby either reservoir may be selectively connected to said second port, which is controlled using an opposed variable control signal which can be varied;

such that when said control signal is greater than a second upper threshold value, said connection means connects said second port to said second reservoir;

whereby said low pressure fluid attempts, through said second actuator, to move said object in said first direction; and such that when said control signal is less than a second lower threshold value, said connection means connects said second port to said first reservoir;

whereby said high pressure fluid attempts, through said second actuator, to move said object in said opposite direction.

18. The control means of claim 17 wherein said primary control signal and said opposed control signal both equal an overall common control signal, whereby said primary and opposed actuators are automatically controlled in concert with one another.

19. The control means of claim 18:

wherein said first and second upper threshold values both equal a common upper threshold value; and wherein said first and second lower threshold values both equal a common lower threshold value;

whereby the ports of said primary and opposed actuators are simultaneously connected to said high and low pressure reservoirs, respectively, when said common control signal exceeds said common upper threshold value;

such that said primary and opposed actuators both attempt to move said object in the same first direction working together in concert; and whereby the ports of said primary and opposed muscle analogs are simultaneously connected to said low and high pressure reservoirs, respectively, when said common control signal falls below said common lower threshold value;

such that said primary and opposed actuators both attempt to move said object in said opposite direction, working together in concert;

whereby said common control signal and reservoirs together form an automatically coordinated control means for controlling said connection means of said actuators and thereby said actuators.

20. The control means of claim 19, further comprising:

a measurement means for measuring the position of said object, which produces a measured positional signal which corresponds to the measured position of said object according to a first predetermined relationship between said position and said signal;

a variable target positional signal which may be varied, representing a target position of said object according to said first predetermined relationship;

whereby if said object is in said target position, said measurement means produces said target signal;

a differential amplifying means with two inputs, for amplifying the difference between two input signals, whose two inputs are said measured positional signal and said target positional signal, and whose output is the amplified difference between them;

wherein said amplifying means has an upper compliance limit and a lower compliance limit which its output cannot exceed; and wherein said amplifying means also has an input sensitivity below which its output does not vary significantly from its value when said input signals are identical;

such that when said target signal and measured signal differ by less than said sensitivity, said output remains the same as if said signals were equal;

whereby said output, being amplified, rapidly approaches said upper compliance limit when said difference, of one polarity, exceeds said sensitivity, and rapidly approaches said lower compliance limit when said difference of the opposite polarity exceeds said sensitivity;

whereby if said output signal forms said common control signal, said target and measured signals may be connected to said inputs with polarity chosen such that both of said actuators act in concert to reduce said difference to below said sensitivity;

whereby an automatic control system for said opposed actuators is formed such that said actuators, in concert with one another, attempt to keep the measured position of said object at said target position, within said sensitivity.

* * * * *